United States Patent
Geall et al.

(10) Patent No.: US 11,291,635 B2
(45) Date of Patent: *Apr. 5, 2022

(54) VIRION-LIKE DELIVERY PARTICLES FOR SELF-REPLICATING RNA MOLECULES

(75) Inventors: Andrew Geall, Littleton, MA (US); Christian Mandi, Lexington, MA (US); Derek O'Hagan, Winchester, MA (US); Manmohan Singh, Cary, NC (US)

(73) Assignee: GLAXOSMITHKLINE BIOLOGICAL SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/808,089

(22) PCT Filed: Jul. 6, 2011

(86) PCT No.: PCT/US2011/043103
§ 371 (c)(1),
(2), (4) Date: Apr. 8, 2013

(87) PCT Pub. No.: WO2012/006376
PCT Pub. Date: Jan. 12, 2012

(65) Prior Publication Data
US 2013/0195968 A1  Aug. 1, 2013

Related U.S. Application Data

(60) Provisional application No. 61/361,828, filed on Jul. 6, 2010.

(51) Int. Cl.
| | | |
|---|---|---|
| *A61K 9/50* | (2006.01) | |
| *A61K 39/155* | (2006.01) | |
| *A61K 39/245* | (2006.01) | |
| *C12N 15/86* | (2006.01) | |
| *C12N 15/88* | (2006.01) | |
| *A61K 39/12* | (2006.01) | |
| *A61K 9/127* | (2006.01) | |
| *A61K 9/00* | (2006.01) | |
| *A61K 39/00* | (2006.01) | |

(52) U.S. Cl.
CPC .............. *A61K 9/50* (2013.01); *A61K 9/0019* (2013.01); *A61K 9/127* (2013.01); *A61K 39/12* (2013.01); *A61K 39/155* (2013.01); *A61K 39/245* (2013.01); *C12N 15/86* (2013.01); *C12N 15/88* (2013.01); *A61K 39/00* (2013.01); *A61K 2039/53* (2013.01); *A61K 2039/55505* (2013.01); *A61K 2039/55555* (2013.01); *A61K 2039/55566* (2013.01); *C12N 2710/16134* (2013.01); *C12N 2760/18522* (2013.01); *C12N 2760/18534* (2013.01); *C12N 2770/36143* (2013.01)

(58) Field of Classification Search
CPC .. A61K 39/12; A61K 38/177; A61K 2039/53; A61K 39/39; A61K 2039/51; A61K 48/00; A61K 2039/58; A61K 2039/70; A61K 2039/55555; A61K 9/127; A61K 9/0019; A61P 31/14
See application file for complete search history.

(56) References Cited

U.S. PATENT DOCUMENTS

| | | |
|---|---|---|
| 5,013,556 A | 5/1991 | Woodle et al. |
| 5,279,833 A | 1/1994 | Rose |
| 5,750,390 A | 5/1998 | Thompson et al. |
| 5,814,482 A | 9/1998 | Dubensky et al. |
| 5,972,704 A | 10/1999 | Draper et al. |
| 6,009,406 A | 12/1999 | Nick |
| 6,015,686 A | 1/2000 | Dubensky |
| 6,060,308 A | 5/2000 | Parrington |
| 6,090,406 A * | 7/2000 | Popescu et al. ............. 424/450 |
| 6,395,302 B1 | 5/2002 | Hennink et al. |
| 6,432,925 B1 | 8/2002 | Hoon et al. |
| 6,610,321 B2 | 8/2003 | Huang et al. |
| 6,790,449 B2 * | 9/2004 | Collins ..................... 424/211.1 |
| 6,858,225 B2 | 2/2005 | Semple et al. |
| 6,890,554 B2 | 5/2005 | Jessee et al. |
| 7,250,404 B2 | 7/2007 | Feigner et al. |
| 7,303,881 B2 | 12/2007 | Huang et al. |
| 7,384,923 B2 | 6/2008 | Gregoriadis |

(Continued)

FOREIGN PATENT DOCUMENTS

| | | |
|---|---|---|
| BR | 112012001666-0 A2 | 9/2019 |
| EP | 0786522 A1 | 7/1997 |

(Continued)

OTHER PUBLICATIONS

Vajdy et al, "Mucosal Adjuvants and Delivery Systems for Protein-, DNA- and RNA-Based Vaccines," Immunology and Cell Biology, vol. 82, No. 6, pp. 617-627 (2004).*
Kulkarni, et al. (1995). Factors affecting microencapsulation of drugs in liposomes. Journal of Microencapsulation, 12 (3), 229-46.
Chiaramoni et al. Liposome/DNA systems: correlation between hydrophobicity and DNA conformational change. J Biol Phys (2008) 34:179-188.
Semple et al. Efficient encapsulation of antisense oligonucleotides in lipid vesicles using ionizable aminolipids: formation of novel small multilamellar vesicle structures. Biochimica et Biophysica Acta (BBA)—Biomembranes, vol. 1510, 2001, pp. 152-166.

(Continued)

*Primary Examiner* — Dennis J Parad
(74) *Attorney, Agent, or Firm* — Christopher L. Wright

(57) ABSTRACT

Nucleic acid immunisation is achieved by delivering a self-replicating RNA encapsulated within a small particle. The RNA encodes an immunogen of interest, and the particle may deliver this RNA by mimicking the delivery function of a natural RNA virus. Thus the invention provides a non-virion particle for in vivo delivery of RNA to a vertebrate cell, wherein the particle comprises a delivery material encapsulating a self-replicating RNA molecule which encodes an immunogen. These particles are useful as components in pharmaceutical compositions for immunising subjects against various diseases.

7 Claims, 11 Drawing Sheets

(56) References Cited

U.S. PATENT DOCUMENTS

| | | |
|---|---|---|
| 7,557,200 B2 | 7/2009 | Wu et al. |
| 7,799,565 B2 | 9/2010 | MacLachlan et al. |
| 8,058,069 B2 | 11/2011 | Yaworski et al. |
| 8,338,583 B2 | 12/2012 | Michaeli |
| 8,877,206 B2 | 11/2014 | Chen et al. |
| 9,254,265 B2 | 2/2016 | Geall et al. |
| 9,504,651 B2 | 11/2016 | MacLachlan et al. |
| 9,770,463 B2 | 9/2017 | Geall et al. |
| 9,801,897 B2 | 10/2017 | Geall et al. |
| 9,801,987 B2 | 10/2017 | Geall et al. |
| 10,487,332 B2 | 11/2019 | Geall |
| 10,532,067 B2 | 1/2020 | Geall et al. |
| 11,026,964 B2 | 6/2021 | Geall et al. |
| 2003/0124134 A1* | 7/2003 | Edwards et al. ............ 424/184.1 |
| 2003/0138453 A1 | 7/2003 | O'Hagan et al. |
| 2003/0212022 A1 | 11/2003 | Vogel et al. |
| 2004/0142025 A1 | 7/2004 | MacLachlan et al. |
| 2005/0032730 A1 | 2/2005 | Von Der Mulbe et al. |
| 2005/0042230 A1* | 2/2005 | Anderson et al. ......... 424/186.1 |
| 2005/0064595 A1 | 3/2005 | Maclachlan et al. |
| 2005/0118566 A1 | 6/2005 | Escriou et al. |
| 2006/0002991 A1 | 1/2006 | Essler et al. |
| 2006/0051405 A1* | 3/2006 | MacLachlan et al. ........ 424/450 |
| 2006/0063732 A1* | 3/2006 | Vogel et al. ..................... 514/44 |
| 2006/0083780 A1 | 4/2006 | Heyes et al. |
| 2006/0177819 A1* | 8/2006 | Smith et al. ........................ 435/5 |
| 2007/0014805 A1 | 1/2007 | Dalencon et al. |
| 2007/0118094 A1 | 5/2007 | Bingham et al. |
| 2008/0057080 A1 | 3/2008 | Luke et al. |
| 2008/0085870 A1 | 4/2008 | Hermanson et al. |
| 2008/0249046 A1 | 10/2008 | MacLachlan et al. |
| 2008/0311158 A1 | 12/2008 | Merola |
| 2009/0104226 A1 | 4/2009 | Perri et al. |
| 2010/0040650 A1* | 2/2010 | Crowe et al. .............. 424/212.1 |
| 2010/0173980 A1 | 7/2010 | Valliant et al. |
| 2011/0020667 A1 | 1/2011 | Deeman et al. |
| 2011/0076335 A1 | 3/2011 | Yaworski et al. |
| 2011/0200582 A1 | 8/2011 | Baryza |
| 2011/0200667 A1 | 8/2011 | Contreras et al. |
| 2011/0244026 A1 | 10/2011 | Guild et al. |
| 2011/0300205 A1 | 12/2011 | Geall |
| 2011/0305727 A1* | 12/2011 | Swanson et al. ........... 424/211.1 |
| 2012/0100207 A1 | 4/2012 | Motokui et al. |
| 2012/0195936 A1 | 8/2012 | Carten et al. |
| 2013/0171241 A1 | 7/2013 | Geall |
| 2013/0189351 A1 | 7/2013 | Geall |
| 2013/0195968 A1 | 8/2013 | Geall et al. |
| 2013/0195969 A1* | 8/2013 | Geall et al. .................... 424/450 |
| 2013/0202684 A1 | 8/2013 | Geall |
| 2014/0141070 A1 | 3/2014 | Geall |
| 2016/0024157 A1 | 1/2016 | Masignani et al. |
| 2016/0129105 A1 | 5/2016 | Mülbe et al. |
| 2018/0094033 A1 | 4/2018 | Telford et al. |
| 2019/0343862 A1 | 11/2019 | Geall et al. |
| 2020/0048636 A1 | 2/2020 | Geall |
| 2020/0323896 A1 | 10/2020 | Geall et al. |
| 2021/0268013 A1 | 9/2021 | Geall et al. |

FOREIGN PATENT DOCUMENTS

| | | | |
|---|---|---|---|
| EP | 1083232 A1 | 3/2001 | |
| EP | 1392341 B1 | 3/2005 | |
| EP | 1637144 A1 | 3/2006 | |
| EP | 2591114 B1 | 6/2016 | |
| EP | 2590676 B1 | 8/2016 | |
| EP | 3318248 B1 | 4/2019 | |
| EP | 2591103 B1 | 8/2019 | |
| JP | 2001514857 A | 9/2001 | |
| JP | 2007-112768 A1 | 5/2007 | |
| JP | 2008501729 A | 1/2008 | |
| WO | 1993024640 A2 | 12/1993 | |
| WO | 98/10748 A1 | 3/1998 | |
| WO | 1999011808 A1 | 3/1999 | |
| WO | 99/52503 A2 | 10/1999 | |
| WO | 00/00617 A2 | 1/2000 | |
| WO | 01/029233 A2 | 4/2001 | |
| WO | 2001/79253 A1 | 10/2001 | |
| WO | 2002002606 A2 | 1/2002 | |
| WO | 02/09645 A2 | 2/2002 | |
| WO | 92/09645 A2 | 2/2002 | |
| WO | 02/026209 A2 | 4/2002 | |
| WO | 2002034771 A2 | 5/2002 | |
| WO | 02/061113 A2 | 8/2002 | |
| WO | 02/072027 A2 | 9/2002 | |
| WO | 02/079239 A2 | 10/2002 | |
| WO | 02/095023 A2 | 11/2002 | |
| WO | 20020269209 A3 | 1/2003 | |
| WO | 2003018054 A1 | 3/2003 | |
| WO | 2003068190 A1 | 8/2003 | |
| WO | 2004098509 A2 | 11/2004 | |
| WO | 2005002619 A2 | 1/2005 | |
| WO | 2005032582 A2 | 4/2005 | |
| WO | 2005111066 A2 | 11/2005 | |
| WO | 2005113782 A1 | 12/2005 | |
| WO | 2005120152 A2 | 12/2005 | |
| WO | 2005121348 A1 | 12/2005 | |
| WO | 06/078294 | 7/2006 | |
| WO | 2006089264 A2 | 8/2006 | |
| WO | 2006091517 A2 | 8/2006 | |
| WO | 2006092607 A1 | 9/2006 | |
| WO | 2006110413 A2 | 10/2006 | |
| WO | 2006138004 A2 | 12/2006 | |
| WO | 2007024708 A2 | 3/2007 | |
| WO | WO2007/047749 | 4/2007 | |
| WO | WO 2007047749 A1 * | 4/2007 | |
| WO | 2007049155 A2 | 5/2007 | |
| WO | 2007024708 A3 | 9/2007 | |
| WO | 2008020330 A2 | 2/2008 | |
| WO | 2008103276 A2 | 8/2008 | |
| WO | 2008/137758 A2 | 11/2008 | |
| WO | 2008/155141 A2 | 12/2008 | |
| WO | 2009016515 A2 | 2/2009 | |
| WO | 2009031043 A2 | 3/2009 | |
| WO | 2009042794 A2 | 4/2009 | |
| WO | 2009/079185 A2 | 6/2009 | |
| WO | 2009086558 A1 | 7/2009 | |
| WO | 2009104092 A2 | 8/2009 | |
| WO | 2009109860 A2 | 9/2009 | |
| WO | 2009111088 A2 | 9/2009 | |
| WO | 2009127230 A1 | 10/2009 | |
| WO | 2009132206 A1 | 10/2009 | |
| WO | 09/146867 A1 | 12/2009 | |
| WO | 2010/015098 A1 | 2/2010 | |
| WO | 2010015098 A1 | 2/2010 | |
| WO | 2010042877 A1 | 4/2010 | |
| WO | 2010059689 A2 | 5/2010 | |
| WO | 2010119343 A2 | 10/2010 | |
| WO | 2011/005799 A2 | 1/2011 | |
| WO | 2011/008974 A2 | 1/2011 | |
| WO | 2011001780 A1 | 1/2011 | |
| WO | 2011008974 A2 | 1/2011 | |
| WO | 2011/068810 A1 | 6/2011 | |
| WO | 2011/076807 A2 | 6/2011 | |
| WO | WO-2011140627 A1 * | 11/2011 | ........... A61K 9/1272 |
| WO | 12/006378 A1 | 1/2012 | |
| WO | 2012/006369 A2 | 1/2012 | |
| WO | 2012/006377 A2 | 1/2012 | |
| WO | 2012/006380 A2 | 1/2012 | |
| WO | 2012006372 A1 | 1/2012 | |
| WO | 12/030901 A1 | 3/2012 | |
| WO | 2012031046 A1 | 3/2012 | |
| WO | WO-2012/031043 * | 3/2012 | |
| WO | 2013033563 A1 | 3/2013 | |

OTHER PUBLICATIONS

Elbashir et al., (2001). Duplexes of 21-nucleotide RNAs mediate RNA interference in cultured mammalian cells. Nature, 411(6836), 494-8.

Geall, A. et al (2012). Nonviral delivery of self-amplifying RNA vaccines. Proceedings of the National Academy of Sciences of the United States of America, 109(36), 14604-9.

(56) References Cited

OTHER PUBLICATIONS

Gonçalves, et al (2004). The effect of liposome size on the final lipid/DNA ratio of cationic lipoplexes. Biophysical Journal, 86(3), 1554-63.
Chrai, et al (2002). Liposomes: A Review Part I: Manufacturing Issues, (April), Biotech Trends, Pharmaceutical Technology, pp. 28-34.
Tseng et al., Liposomes incorporated with cholesterol for drug release triggered by magnetic field, Journal of Medical and Biological Engineering, vol. 27, No. 1 (2007), 29-34.
Ramana, et al (2010). Development of a liposomal nanodelivery system for nevirapine. Journal of Biomedical Science, 17, 57.
Samad et al (2007). Liposomal drug delivery systems: an updated review. Curr Drug Deliv. Oct. 2007;4(4):297-305.
Silva, et al (2010). Effect of ultrasound parameters for unilamellar liposome preparation. Ultrasonics Sonochemistry, 17 (3), 628-32.
Mockey, M., et al., "mRNA-based cancer vaccine: prevention of B16 melanoma progression and metastasis by systemic injection of MART1 mRNA histidylated lipopolyplexes", Cancer Gene Therapy, 14(9): 802-814 (2007)—XP055007324.
El Ouahabi, A. et al., "Double long-chain amidine liposome-mediated self replicating RNA transfection", FEBS Letters, 380(1-2): 108-112 (1996)—XP002660043
Levine, M., et al., "Vaccine development strategies for improving immunization: the role of modern immunology", Nature Immunol., 5(5): 460-464 (2004)—XP002660044.
Cannon, G., et al., "RNA Based Vaccines", DNA Cell Biol., 21(12): 953-961 (2002)—XP002660046.
Zhou, W.Z., et al., "RNA Melanoma Vaccine: Induction of Antitumor Immunity by Human Glycoprotein 100 mRNA Immunization", Human Gene Therapy, 10(16): 2719-2724 (1999).
Saeki, Y., et al., "Development and Characterization of Cationic Liposomes Conjugated with HVJ (Sendai Virus): reciprocal Effect of Cationic Lipid for in Vitro and in Vivo Gene Transfer", Human gene Therapy, 8(17): 2134-2135 (1997).
Martinon, F, et al., "Inductions of virus-specific cytotoxic T lymphocytes in vivo by liposome-entrapped mRNA", Eur. J. Immunol. 23: 1719-1722 (1993).
Fleeton et al. "Self-Replicative RNA Vaccines Elicit Protection against Influenza A Virus, Respiratory Syncytial Virus a and Tickborne Encephalitis Virus", Journal of Infectious Diseases 183:1395-1398 (2001).
Yamamoto, et al. "Current prospects for mRNA gene delivery". Eur. J. of Pharma and Biopharm 71, 484-489. (2009).
Zhang, J., et al., "Ionization Behavior of Amino Lipids for siRNA Delivery: Determinationof Ionization Constants, SAR, and the Impact of Lipid pKa on CationicLipid-Biomembrane Interactions," Langmuir: The ACS Journal of Surfaces and Colloids , ACS, 15:5, 1907-1914 (2011).
Kita, H. et al. "Replication of Genetic Information with Self-Encoded Replicase in Liposomes" Chembiochem 9 (15) 2403-2410 (2008).
Stuart, et al, "A new liposomal formulation for antisense oligodeoxynucleotides with small size, high incorporation efficiency and good stability", Biochimica et Biophysica Acta, 1463(2), 219-29 (2000).
Lonez, C. et al., "Cationic liposomal lipids: From gene carriers to cell signaling", Progress in Lipid Research, 47 (5):340-347 (2008).
Caplen, N. J., "Nucleic acid transfer using cationic lipids", Methods in Mole. Biol., 133:1-19 (2000).
Hoerr et al. "In vivo application of RNA leads to induction of specific cytotoxic T lymphocytes and antibodies" Eur. J. Immunol. 30:1-7 (2000).
Leitner et al. "DNA and RNA-based vaccines: principles, progress and prospects" Vaccine 18:765-77 (1999).
Vajdy et al., "Mucosal adjuvants and delivery systems for protein-, DNA- and RNA-based vaccines." Immunol Cell Biol. Dec. 2004;82(6):617-27.
Vassilev et al. "Microparticle-mediated RNA immunization against bovine viral diarrhea virus" Vaccine 19:2012-19 (2001).

Ying et al. "Cancer therapy using a self-replicating RNA vaccine" Nat. Med. 5:823-27(1999).
Barai, V.N. et al. Production of highly purified RNA from yeast using calcium. Applied Biochemistry and Microbiology. 1995; 31(5): 421-424.
Gamvrellis A. et al. Vaccines that facilitate antigen entry into dendritic cells. Immunol Cell Biol. Oct. 2004; 82(5): 506-516.
Wang, et al., "pH-sensitive immunoliposomes mediate target-cell-specific delivery and controlled expression of a foreign gene in mouse." Proc. Natl. Acad. Sci. USA; 1987; pp. 7851-7855; vol. 84.
Felgner, et al., "Lipofection: A highly efficient, lipid-mdiated DNA-transfection procedure." Proc. Natl. Acad. Sci. USA; 1987; pp. 7413-7417; vol. 84.
Declaration of Prof. Liljestrom submitted to the European Patent Office in the opposition proceedings concerning EP2590676 B1.
Yoder, et al., "Role of Complement in Neutralization of Respiratory Syncytial Virus" J Med Virol; 2004; pp. 688-694; vol. 72.
Smerdou, et al.,"Non-viral amplification systems for gene transfer: Vectors based on alphaviruses." Curr Opin Mol Ther; 1999; pp. 244-251; vol. 1(2).
Maurer, et al., "Spontaneous Entrapment of Polynucleotides upon Electrostatic Interaction with Ethanol-Destabilized Cationic Liposomes" Biophys J; 2001; pp. 2310-2326; vol. 80.
Papahadjopoulos, et al., "Cochleate Lipid Cylinders: Formation by Fusion of Unilamellar Lipid Vesicles" Biochim et Biophys Acta; 1975; pp. 483-491; vol. 394.
Papahadjopoulos, et al., "Incorporation of Macromolecules within Large Unilamellar Vesicles (LUV)" Annals NY Academy of Sciences; 1978; pp. 259-267.
Atwood, et al., "Comprehensive Supramolecular Chemistry II" Gen. Prin. of SupraMol. Chem. and Mol. Recogn.; pp. 141-143.
Freddolino, et al, "Molecular Dynamics Simulations of the Complete Satellite Tobacco Mosaic Virus." Structure; 2006; pp. 437-449; vol. 14.
Lyubchenko, et al., "Visualization of supercoiled DNA with atomic force microscopy in situ" Proc. Natl. Acad Sci. USA; 1997; pp. 496-501; vol. 94.
BMGF Report 2012.
Aberle, "Humoral and Cellular Immune Response to RNA Immunization with Flavivirus Replicons Derived from Tick-Borne Encephalitis Virus" Journal of Virology; 2005; pp. 15107-15113; vol. 79(24).
Bringmann, et al., RNA Vaccines in Cancer Treatment; J Biomedicine and Biotechnology; Epub. Jun. 1, 2010; pp. 1-12.
Brito, "Cationic Nanoemulsion for the delivery of next-generation RNA vaccines" Molecular Therapy, 2014; pp. 2118-2129; vol. 22.
Buyens, "Elucidating the Encapsulation of Short Interfering RNA in PEGylated Cationic Liposomes", Langmuir; 2009; pp. 4886-4891; vol. 25, No. 9.
Fenske, "Liposomal Nanomedicines: An Emerging Field", Toxicologic Pathology; 2008; pp. 21-29; vol. 36, No. 1.
Fraenkel-Conrat, "Togaviridae", Virology second edition, Prentice-Hall Inc.; 1988; p. 2 pp. 99.
Geisbert, et al., 2006, "Postexposure Protection of Guinea Pigs against a Lethal Ebola Virus Challenge Is Conferred by RNA Interference" Journal of Infectious Diseases; 2006; pp. 1650-1657; vol. 193.
Heyes,et al., 2005, "Cationic lipid saturation influences intracellular delivery of encapsulated nucleic acids" J Control Release; 2005; pp. 276-287; vol. 107.
Jeffs, et al.,"A scalable, extrusion-free method for efficient liposomal encapsulation of plasmid DNA" Pharm Res; 2005; pp. 362-372; vol. 22(3).
Knipe; Fields Virology, 4th edition, Lipincott Williams & Wilkins, 2001; pp. 690; vol. 1, p. 2.
Levy; "Quantitation of supercoiled circular content in plasmid DNA solutions using a fluorescence based method" Nucleic Acids Res.; 2000; 28:e57.
Lundstrom et al., "Biology and application of alphaviruses in gene therapy", Gene Therapy; 2005; Suppl 1; pp. S92-S97.
Manning and Millson, "Infectivity of Liposomally Encapsulated Nucleic Acids Isolated From EMC Virus and Scrapie-Infected Mouse Brain", Intervirology; 1983; pp. 164-168; vol. 20.

(56) References Cited

OTHER PUBLICATIONS

Obata, "Evaluation of pH-responsive liposomes containing amino acid-based zwitterionic lipids for improving intracellular drug delivery in vitro and in vivo", Journal of Controlled Release; 2010; pp. 267-276; vol. 142, No. 2.
Rayner, et al., "Alphavirus vectors and vaccination", Reviews in Medical Virology; 2002; pp. 279-296; vol. 12.
Ren, et al., "Immunogene therapy of recurrent glioblastoma mult/forme with a liposomally encapsulated replication-incompetent Semliki forest virus vector carrying the human interleukin-12 gene—a phase //11 clinical protocol", Journal of NeuroOncology; 2003; pp. 147-154; vol. 64.
Saxena et al., "Induction of immune responses and protection in mice against rabies using a self-replicating RNA vaccine encoding rabies virus glycoprotein" Veterinary Microbiology; 2009; pp. 36-44; vol. 136(1-2).
Schirrmacher, et al., "Intra-pinna anti-tumor vaccination with self-replicating infectious RNA or with DNA encoding a model tumor antigen and a cytokine" Gene Therapy; 2000; pp. 1137-1146; vol. 7.
Strejan, "Suppression of Chronic-Relapsing Experimental Allergic Encephalomyelitis in Strain-13 Guinea Pigs by Administration of Liposome-Associated Myelin Basic Protein", Journal of Neuroimmunology; 1984; pp. 27-41; vol. 7.
Textbook "Antisense Drug Technology", Crooke, 2nd ed. CRC Press 2008, pp. 237-270, chapter 9: "Liposomal Formulations for Nucleic Acid Delivery".
Vignuzzi, "Naked RNA immunization with replicons derived from poliovirus and Semliki Forest virus genomes for the generation of a cytotoxic T cell response against the influenza A virus nucleoprotein", Journal of General Virology; 2001; pp. 1737-1747; vol. 82, No. 7.
Wang and Huang, "pH-sensitive immunoliposomes mediate target-cell-specific delivery and controlled expression of a foreign gene in mouse", Proc. Nat. Acad. Sci. USA, 1987; pp. 7851-7855; vol. 84.
Whitehead, et al., "Knocking down barriers: advances in siRNA delivery" Nature Reviews Orug Oiscovery; 2009; pp. 129-138; vol. 8.
Wilson, "Biological properties of poliovirus encapsulated in lipid vesicles: Antibody resistance and infectivity in virus-resistant cells", Proc. Natl. Acad. Sci. USA; 1977; pp. 3471-3475; vol. 74, No. 8.
Wilson,"The Introduction of Poliovirus RNA into Cells via Lipid Vesicles (Liposomes)", Cell; 1979; pp. 77-84; vol. 17.
Yoffe, "Predicting the sizes of large RNA molecules" PNAS; 2008; pp. 16153-16158; vol. 105.
Zimmermann, et al., "RNAi-mediated gene silencing in non-human primates" Nature; 2006; pp. 111-114; vol. 441.
U.S. Appl. No. 61/361,828, filed Jul. 6, 2010.
U.S. Appl. No. 61/280,510, filed Nov. 4, 2009, Cullis et al.
Rodriguez-Gascon, A. et al., "Development of nucleic acid vaccines: use of self-amplifying RNA in lipid nanoparticles," International Journal of Nanomedicine, 9:1833-1843 (2014).
Evers, M., Kulkarni, J., Van Der Meel, R., Cullis, P., Vader, P., Schiffelers, R., "State-of-the-Art Design and Rapid-Mixing Production Techniques of Lipid Nanoparticles for Nucleic Acid Delivery" Small Methods, 2:1-20, (2018).
Crooke Stanley T. ed., Antisense Drug Technology: Principles, Strategies, and Applications, 2nd ed., chapter 9 (2008), pp. 237-270.
Schlesinger and Dubensky Curr. Op. Biotech, 1999, vol. 10, pp. 434-439.
SINGH et al. PNAS, 97:811-816 (2000).
Ott et al., Journal of Controlled Release, 79:1-5 (2002).
Certified Copy of U.S. Appl. No. 61/361,794, filed Jul. 6, 2010.
Zuckerman, BMJ, 321:1237-1238 (2000).
Zhou et al., Human Gene Therapy, 10:2719-2724 (1999).
Wilson et al., Cell, 17:77-84 (1979).
Heyes et al., Journal of Controlled Release, 107:276-287 (2005).
Lazzaro et al., Immunology, 146:312-326 (2015).
Anonymous, "Mengovirus", Wikipedia, (Apr. 25, 2020), pp. 1-2, URL: https://en.wikipedia.org/wiki/Mengovirus.
Leitner et al., Vaccine, 18:765-777 (2000).
Dupuis et al., Cellular Immunology, 186:18-27 (1998).
Dupuis et al., Journal of Immunology, 165:2850-2858 (2000).
Mosca et al., Proc. Natl. Acad. Sci. USA, 105:10501-10506 (2008).
Kumar et al., Biochemical and Biophysical Research Communications, 388:621-625 (2009).
Jeffs et al., Pharmaceutical Research, 22:362-372 (2005).
Cheng et al., Journal of Immunology, 166:6218-6226 (2001).
611223347 Jul. 6, 2009; U.S. Certified Provisional Patent Application.
Acheampong, Samuel et al.; "Ionization and transfection activity of n-methyl-substituted carbamoyl-cholesterol derivatives". Journal of Biophysical Chemistry, vol. 2, No. 2, 53-62; 2011.
Herweijer et al. (Advanced Drug Delivery Reviews 27; 1997; 5-16).
Hope, et al., Chapter 8: Reduction of Liposome Size and Preparation of unilamellar Vesicles by Extrusion Techniques. Liposome Technology; 1993; pp. 123-129; vol. 1.
Babiuk, S., et al., "Electroporation improves the efficacy of DNA vaccines in large animals." Vaccine; pp. 3399-3408 Vol. 20(27-28).
Bagarazzi, M. L., et al., "Immunotherapy against HPV16/18 generates potent TH1 and cytotoxic cellular immune responses." Science Translational Medicine; 2012; vol. 4(155).
Bailey et al., Biochemistry, 33:12573-80 (1994).
Birdi, K.S., Handbook of Surface and Colloidal Chemistry, CRC Press.
Bogers, et al., "Macaques Primed with Self-Amplifying RNA Vaccines Expressing HIV-1 Envelope and Boosted with Recombinant Protein Show Potent T- and B-Cell Responses" poster at the AIDS Vaccine 2012 meeting; Sep. 9-12, 2012; Boston, MA USA.
Bogers, et al., "Potent Immune Responses in Rhesus Macaques Induced by Nonviral Delivery of a Self-amplifying RNA Vaccines Expressing HIV Type 1 Envelope With a Cationic Nanoemulsion." J. Infectious Disease; 2015; pp. 947-955; vol. 211.
Boxus, M., et al., "DNA immunization with plasmids encoding fusion and nucleocapsid proteins of bovine respiratory synctial virus induces a strong cell-mediated immunity and protects calves against challeng." Journal of Virology; 2007 pp. 6879-6889; vol. 81(13).
Bramwell (DDT. 2005; 10(22): 1527-1534).
Brito, Luis et al.; "Self-Amplifying mRNA Vaccines", Advances in Genetics, vol. 89; pp. 179-233; 2014.
Broz, et al. "Newly described pattern recognition receptors team up against intracellular pathogents", Nat. Rev. Immunol. 13:8: 551-565 (2013).
Buza, J. et al., "CD14+ cells are required for IL-12 response in bovine blood mononuclear cells activated with Toll-like receptor (TLR) 7 and TLR8 ligands", Vet. Immunol. Immunopath. 126(3-4): 273-282 (2008)—XP025676816.
Carralot, J.P., et al., "Polarization of immunity induced by direct injection of naked sequence-stabilized mRNA vaccines", Cell. Mole. Life Sci. 61(18): 2418-2424 (2004)-XP002355208.
Chambers, et al., "Vaccination of mice and cattle with plasmid DNA encoding the Mycobacterium bovis antigent MPB83." Clinical Infection Diseases; 2000; pp. S283-S287; vol. 30(3).
Cheng, W.F., et al., "Enhancement of Sindbis Virus Self-Replicating RNA Vaccine Potency by Linkage of Herpes Simplex Virus Type 1 VP22 Protein to Antigen", J. Viral. 75(5): 2368-2376 (2001)-XP002201711.
Hornung, et al., "5'-Triphosphate RNA Is the Ligand for RIG-I" Science; 2006; vol. 314; pp. 994-997.
Conry, et al., "Characterization of a Messenger RNA Polynucleotide Vaccine Vector." Cancer Research; 1995; pp. 1397-1400; vol. 55.
Cox, et al., "Bovine herpesvirus 1: immune responses in mice and cattle injected with plasmid DNA." Journal of Virology; 1993; pp. 5664-5667; vol. 67(9).
Cui, et al., DNA Vaccine, Advances in Genetics; 2005; pp. 257-289; vol. 54.
Cvagna, et al.; "7—Signs and Work of Man"; The National Park of the Casentine Forests; 2003; p. 175.
Davis, et al., "DNA vaccine for hepatitis B Evidence for immunogenicity in chimpanzees and comparison with other vaccines." Proc. Natl Acad Sci USA; 1996; pp. 7213-7218; vol. 93.
Deering, et al., "Nucleic acid vaccines: prospects for non-viral delivery of mRNA vaccines." Expert Opinion Drug Delivery; 2014; pp. 885-899; vol. 11(6).

(56) References Cited

OTHER PUBLICATIONS

Declaration of Professor Liljestrom dated Dec. 11, 2018 submitted in EP2590676, itself having annexes A-G.
Declaration by Prof. Peter Liljestrom, dated Aug. 7, 2018.
Declaration by Prof. Peter Liljestrom, dated Mar. 31, 2019.
Declaration Andrew Geall dated Sep. 11, 2014.
Huang, et al., Immunization with a bovine herpesvirus 1 glycoprotein B DNA vaccine induces cytotoxic T-lymphocyte responses in mice and cattle. Journal of General Virology; 2005; pp. 887-898; vol. 86(4).
Diebold, S.S., et al., "Innate Antiviral Responses by Means of TLR7-Mediated Recognition of Single-Stranded RNA", Science 303(5663): 1529-1531 (2004).
"Encyclopedia Britannica" House Mouse; 2005.
Excerpt from "Comprehensive Supermolecular Chemistry II" 2017; vol. 1.
Final Decision and Upheld Claims from EP2591114, European Equivalent of U.S. Appl. No. 13/808,153, dated Nov. 27, 2018.
Fynan, E.F., et al., DNA vaccines: Protective immunizations by parenteral, mucosal, and gene-gun inoculations; Proc Natl Acad Sci.; 1993; pp. 11478-11482; vol. 90.
Geall, et al. "Using self-amplifying mRNA vaccines to facilitate a rapid response to pandemic influenza" Eur. Pharm. Review 19:3 20-23 (2014).
Iavarone et al., "A Point Mutation in the Amino Terminus of TLR7 Abolishes Signaling without Affecting Ligand Binding", JIMMUNOL, (2011), vol. 186, pp. 4213-4222.
Giuliani et al., Proc Natl Acad Sci USA, (2006), vol. 103, No. 29, p. 10834-9.
Graham, et al., "Priming Immunization Determines T Helper Cytokine mRNA Expression Patterns in Lungs of Mice Challenged with Respiratory Syncytial Virus." The Journal of Immunology; Aug. 15, 1993; pp. 2032-2040; vol. 151, No. 4.
Granstein, et al., "Induction of Anti-Tumor Immunity with Epidermal Cells Pulsed with Tumor-Derived RNA or Intradermal Administration of RNA." Journal of Investigative Dermatology; 2000; pp. 632-636; vol. 114(4).
Greer, C, et al., "A chimeric alphavirus RNA replicon gene-based vaccine for human parainfluenza virus type 3 induces protective immunity against intranasal virus challenge", Vaccine 25(3): 481-489 (2007)-XP005798901.
"Imagines Immunization" Merriam Webster's Medical Desk Dictionary; 1993; pp. 326-327.
Hamm et al., International Immunology, 2007, vol. 19; 297-304.
Heidel, J.D., et al.,"Administration in non-human primates of escalating intravenous doses of targeted nanoparticles containing ribonucleotide reductase subunit M2 siRNA" Proc. Natl Acad Sci USA; 2007; pp. 5715-5721; vol. 104(14).
Weide, et al., "Direct Injection of Protamine-protected mRNA: Results of a Phase 1/2 Vaccination Trial in Metastatic Melanoma Patients." Journal of Immunotherapy; 2009; pp. 498-507; vol. 32(5).
Patentee's Reply to Opposition in relation to European Patent No. 2591103B1 (Appln No. 11736498.4) dated Oct. 23, 2020 (28 pages).
Wilson, Kaley et al.; "The combination of stabilized plasmid lipid particles and lipid nanoparticle encapsulated CpG containing oligodexoynucleotides as a systemic genetic vaccine", The Journal of Gene Medicine; 11; pp. 14-25; 2009.
Wloch, et al., "Safety and Immunogenicity of A Bivalent of CMV DNA Vaccine in Healthy Adult Subjects." J Infect Dis; 2008; pp. 1634-1642; vol. 197(12).
Xiong et al., Science, 243:1188-1191 (1989).
Yi, et al., "A Cationic Lipid Emulsion/DNA Complex as a Physically Stable and Serum-Resistant Gene Delivery." Pharmaceutical Research; 2000; pp. 314-320; vol. 17.
Yoneyama, Fujita, Cytokine & Growth Factor Reviews, (2007), vol. 18, pp. 545-551.
Yoon, et al., " DNA-Mediated Immunization of Mice with Plasmid Encoding HBs Antigen." J. Korean Med Sci; 1999; pp. 187-192; vol. 14.
Zhou, X., et al., "Self-replicating Semliki Forest virus RNA as recombinant vaccine", Vaccine 12(16): 1510-1514 (1994).
Zuckerman, Principles and Practice of Travel Medicine; 2001; p. 168.
Notice of Opposition in relation to European Patent No. 2591103B1 (Appln No. 11736498.4) dated May 27, 2020 (17 pages).
Notice of Opposition in relation to European Patent No. 2591103B1 (Appln No. 11736498.4) dated May 28, 2020 (44 pages).
U.S. Appl. No. 61/265,653, filed Dec. 1, 2009.
U.S. Appl. No. 61/361,780, filed Jul. 6, 2010.
U.S. Appl. No. 17/560,019, filed Dec. 22, 2021.
U.S. Appl. No. 17/560,052, filed Dec. 22, 2021.
U.S. Appl. No. 17/560,059, filed Dec. 22, 2021.
U.S. Appl. No. 17/560,116, filed Dec. 22, 2021.
U.S. Appl. No. 17/560,138, filed Dec. 22, 2021.
U.S. Appl. No. 17/560,092, filed Dec. 22, 2021.
U.S. Appl. No. 17/511,762, filed Oct. 27, 2021.
U.S. Appl. No. 17/512,258, filed Oct. 27, 2021.
Johanning et al., Nucleic Acids Res, (1995), vol. 23, pp. 1495-1501.
Johnson, T, et al., "TLR9 agonist, but not TLR7/8, functions as an adjuvant to diminish FI-RSV vaccine-enhanced disease, while either agonist used as therapy during primary RSV infection increases disease severity", Vaccine 27 (23): 3045-3052 (2009).
Johnson signed Declaration dated Oct. 22, 2020 (9 pages).
Kariko, et al., "mRNA Is an Endogenous Ligand for Toll-like Receptor 3*"; The Journal of Biological Chemistry; 2004; vol. 279, No. 13; pp. 12542-12550.
Kariko, et al., "Suppression of RNA Recognition by Toll-like Receptors: The Impact of Nucleoside Modification and the Evolutionary Origin of RNA"; Immunity; 2005; vol. 23; pp. 165-175.
Khan, K. H." Review DNA vaccines roles against diseases." Germs; 2013; pp. 26-35; vol. 3(1).
Kinnan, et al., "Enhanced Immunogenicity to Mycobacterium tuberculosis by Vaccination with an Alphavirus Plasmid Replicon Expressing Antigen 85A" Infection and Immunity; 2003; pp. 575-579; vol. 71(1).
Kofler, et al. "Mimicking live flavivirus immunization with a noninfectious RNA vaccine." Proc. Natl. Acad. Sci. USA 2004; pp. 1951-1956; vol. 101(7).
Kornbluth et al. (Journal of Leukocyte Biology, 2006, vol. 80, pp. 1084-1102).
Kutzler, et al., "DNA vaccines; ready for prime time?" Nature Reviews; Genetics; 2008; pp. 776-788; vol. 9(10).
Lee, et al., "Venezuelan Equine Encephatlitis Virus-Vectored Vaccines Protect Mice Against Anthrax Spore Challenge." Infection and Immunity; 2003; pp. 1491-1496; vol. 71.
Liljestrom, et al., (Journal of Virology. Aug. 1991; 65(8): 4107-4113).
Liljestrom, et al., Biotechnology, 9:1356-1361 (1991).
Ljungberg et al., Increased Immunogenicity of a DNA-Launched Venezuelan Equine Encephalitis Virus-Based Replicon DNA Vaccine. Journal of Virology, Dec. 2007, pp. 13412-13423.
Lu, et al. Cancer Gene Ther., 1(4):245-252 (1994) (abstract).
Malone et al., "Cationic liposome-mediated RNA transfection", Proc. Natl. Acad. Sci. (PNAS) USA: Biochemistry; 86:16; 6077-6081; 1989.
Martin, et al., "Characterization of formaldehyde-inactivated poliovirus preparations made from live-attenuated strains" Journal of General Virology; 2003; pp. 1781-1788; vol. 84.
McGlone, et al., "Pig Production: Biological Principles and Applications" Chapter 8; 2000; p. 99.
Merriam-Webster definition of "virion" (downloaded Mar. 14, 2016).
Mockey et al., "mRNA-based cancer vaccine: Prevention of B16 melanoma progressionand metastasis by systemic Injection of MART1 mRNA histidylated lipoplexes". International Journal of Nanomedicine, 2008, 3(3), 359-371.
Morris-Downes, et al., "A recombinant Semliki Forest virus particle vaccine encoding the prME and NS1 proteins of louping ill virus is effective in a sheep challenge model" Vaccine; 2001; pp. 3877-3884; vol. 19.

(56) References Cited

OTHER PUBLICATIONS

Mossman, "Protection against Lethal Simian Immunodeficiency Virus SIVsmmPBj14 Disease by a Recombinant Semliki Forest Virus gp160 Vaccines and by a gp120 Subunit Vaccine." J. Virology; 1996; pp. 1953-1960; vol. 70.
NCBI reference sequence. Homo sapiens coagulation factor VIII (FB), transcript variant 1, mRNA. Mar. 2016, pp. 1-18.
Weide, et al., "Results of the First Phase I/II Clinical Vaccination Trial with Direct Injection of mRNA." Journal of Immunotherapy; 2008; pp. 180-188; vol. 31(2).
O'Hagan et al., J Virology, (2001), vol. 75, pp. 9037-9043.
Opposition Document D60—Johnson Declaration from EP2591114, European Equivalent of U.S. Appl. No. 13/808,153, filed Aug. 8, 2018.
Organism overview of Encephalomyocarditis virus and of Poliovirus obtained from PubMed "Encephalomyocarditis virus." retrieved on Jun. 4, 2019 from https://www.ncbi.nlm.mih.gov/genome/?term=encephalomyocarditis+virus, and "Enterovirus C" retrieved on Jun. 4, 2019 from https://www.ncbi.nlm.nih.gov/genome/?term=poliovirus[orgn].
Perri et al., J Virol, (2003), vol. 77, pp. 10394-10403.
Preliminary Opposition Opinion from EP2591114, European Equivalent of U.S. Appl. No. 13/808,153, dated Feb. 23, 2018.
"Pschyrembel, Klinisches Wortenbuch" Immunisiserung, Immunreaktion; 1997; pp. 747-748.
Ulmer, et al., "Heterologous Protection Against Influenza by Injection of DNA Encoding a Viral Protein." Science; 1993; pp. 1745-1749; vol. 259.
Vasiljeva et al., Journal of Biological Chemistry, Jun. 9, 2000; 275(23):17281-17287.
Ward, et al., "Generation of CTL responses using Kunjin replicon RNA" Immunology and Cell Biology; 2003; pp. 73-78; vol. 81(1).
Sacco, et al., "The Average Body Surface Area of Adult Cancer Patients in the UK: A Multicentre Retrospective Study." PLoS ONE; 2010; pp. 1-6; vol. 5(1).
Saenz-Badillos, et al., "RNA as a tumor vaccine; a review of the literature", Experimental Dermatology; 2001; pp. 143-154; vol. 10, Issue 3.
Third Party Observations under Art. 115 EPC Nov. 3, 2016; pp. 1-17.

Scheel, et al., "Toll-like receptor-dependent activation of several human blood cell types by protamine-condensed RNA"; European Journal of Immunology; 2005; pp. 1557-1566.
Semple et al., Nature Biotechnology, 28:172-176 (2010).
Sharma, et al., "To scale or not to scale: the prinicples of dose extrapolation." British Journal of Pharmacology; 2009 pp. 907-921; vol. 157.
Singh et al., Pharmaceutical Research, (2003), vol. 20, pp. 247-251.
Stability data of licensed vaccines as of Nov. 29, 2012.
Sugiyama, T., "Immunoadjuvant effects of polyadenylic:polyuridylic acids through TLR3 and TLR7", Int. Immunolo. 20 (1 ): 1-9 (2008)-XP002665154.
Taylor, et al., "DNA vaccination against respiratory syncytial virus in young calves." Vaccine; 2005; pp. 1242-1250 vol. 23(10).
Opponents arguments by Georg Schnappauf filed on Jan. 14, 2022 in opposition to European Patent No. 2591103.
Opponents arguments by Janssen Vaccines & Prevention B.V. filed on Jan. 14, 2022 in opposition to European Patent No. 2591103.
Auxilliary requests 1, 2 and 3 (claims 1-13) filed in relation to the Opposition of European Patent No. 2590676B1 (Appln No. 11741348.4) (6 pages).
Szoka, Francis, and Demetrios Papahadjopoulos. "Procedure for preparation of liposomes with large internal aqueous space and high capture by reverse-phase evaporation." PNAS 75.9 (1978): 4194-4198.
ThermoFisher—Ribosomal RNA Sizes.
Lorenzi, Julio CC, et al. "Intranasal vaccination with messenger RNA as a new approach in gene therapy: use against tuberculosis." BMC Biotechnology 10.1 (2010): 1-11.
Smith Korsholm, Karen, et al. "The adjuvant mechanism of cationic dimethyldioctadecylammonium liposomes." Immunology 121.2 (2007): 216-226.
Espuelas, Socorro, et al. "Effect of synthetic lipopeptides formulated in liposomes on the maturation of human dendritic cells." Molecular Immunology 42.6 (2005): 721-729.
Communication of the Board of Appeals pursuant to Art. 15(1) of the Rules of Procedure of the Boards of Appeal Issued on Mar. 25, 2021 in European Patent Application Publication No. 2590676.
Jones et al. "DNA vaccination protects against an influenza challenge in a double-blind randomised placebo-controlled phase 1b clinical trial" Vaccine 27 (2009): 2506-2512.

* cited by examiner

FIGURE 13
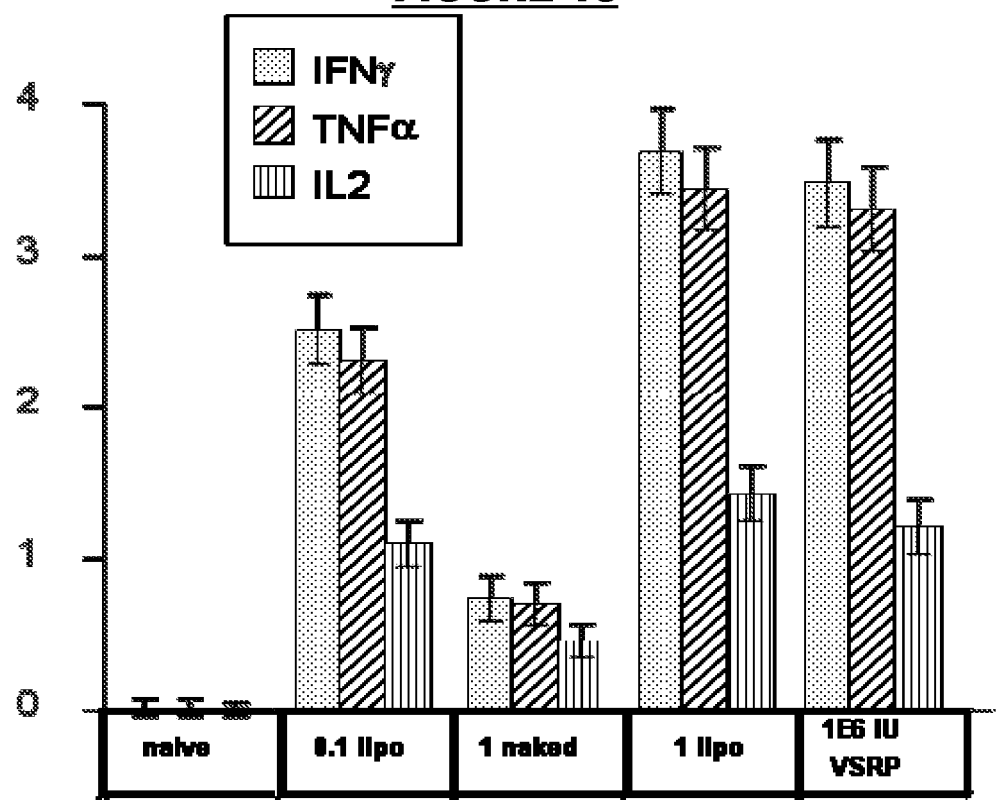
FIGURE 14
FIGURE 14A
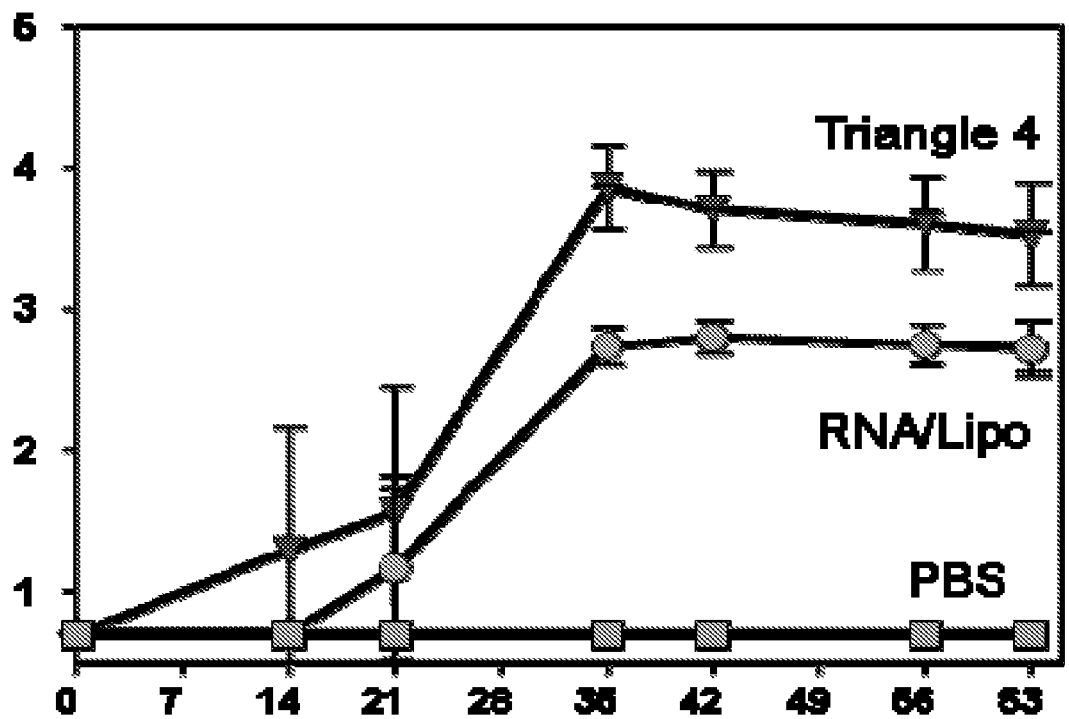

FIGURE 17
FIGURE 17A
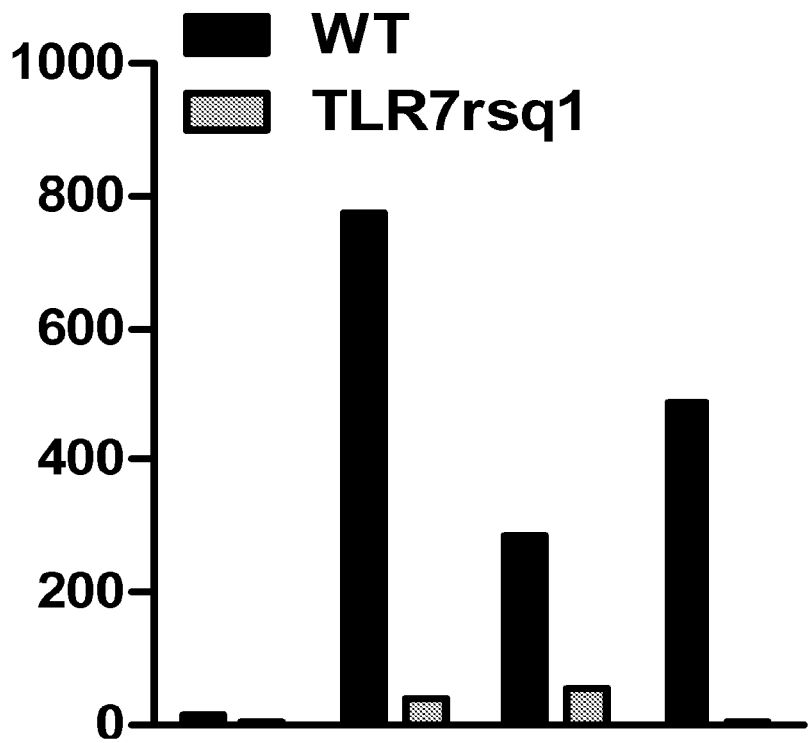
FIGURE 17B
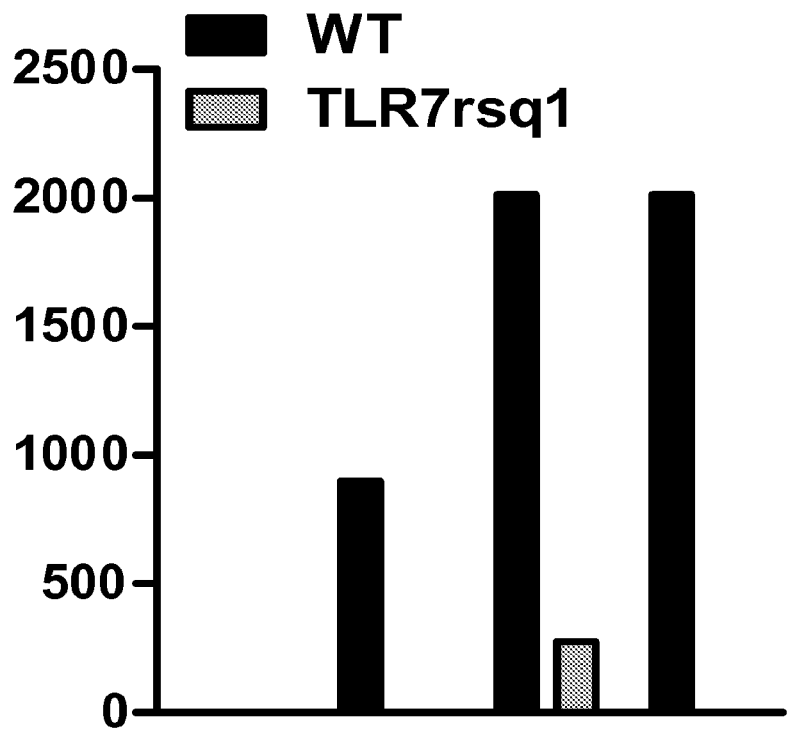

VIRION-LIKE DELIVERY PARTICLES FOR SELF-REPLICATING RNA MOLECULES

This application is the U.S. National Phase of International Application No. PCT/US2011/043103, filed Jul. 6, 2011 and published in English, which claims the benefit of US Provisional Application No. 61/361,828, filed Jul. 6, 2010, the complete contents of which are hereby incorporated herein by reference for all purposes.

TECHNICAL FIELD

This invention is in the field of non-viral delivery of self-replicating RNAs for immunisation.

BACKGROUND ART

The delivery of nucleic acids for immunising animals has been a goal for several years. Various approaches have been tested, including the use of DNA or RNA, of viral or non-viral delivery vehicles (or even no delivery vehicle, in a "naked" vaccine), of replicating or non-replicating vectors, or of viral or non-viral vectors.

There remains a need for further and improved nucleic acid vaccines and, in particular, for improved ways of delivering nucleic acid vaccines.

DISCLOSURE OF THE INVENTION

According to the invention, nucleic acid immunisation is achieved by delivering a self-replicating RNA encapsulated within and/or adsorbed to a small particle. The RNA encodes an immunogen of interest, and the particle may deliver this RNA by mimicking the delivery function of a natural virus.

Thus the invention provides a non-virion particle for in vivo delivery of RNA to a vertebrate cell, wherein the particle comprises a delivery material encapsulating a self-replicating RNA molecule which encodes an immunogen. The invention also provides a non-virion particle for in vivo delivery of RNA to a vertebrate cell, wherein the particle comprises a delivery material on which a self-replicating RNA molecule which encodes an immunogen is adsorbed. These particles are useful as components in pharmaceutical compositions for immunising subjects against various diseases. The combination of utilising a non-virion particle to deliver a self-replicating RNA provides a way to elicit a strong and specific immune response against the immunogen while delivering only a low dose of RNA. Moreover, these particles can readily be manufactured at a commercial scale.

The Particle

Particles of the invention are non-virion particles i.e. they are not a virion. Thus the particle does not comprise a protein capsid. By avoiding the need to create a capsid particle, the invention does not require a packaging cell line, thus permitting easier up-scaling for commercial production and minimising the risk that dangerous infectious viruses will inadvertently be produced.

Instead of encapsulating RNA in a virion, particles of the invention are formed from a delivery material. Various materials are suitable for forming particles which can deliver RNA to a vertebrate cell in vivo. Two delivery materials of particular interest are (i) amphiphilic lipids which can form liposomes and (ii) non-toxic and biodegradable polymers which can form microparticles. Where delivery is by liposome, RNA should be encapsulated; where delivery is by polymeric microparticle, RNA can be encapsulated or adsorbed. A third delivery material of interest is the particulate reaction product of a polymer, a crosslinker, a RNA, and a charged monomer.

Thus one embodiment of a particle of the invention comprises a liposome encapsulating a self-replicating RNA molecule which encodes an immunogen, whereas another embodiment comprises a polymeric microparticle encapsulating a self-replicating RNA molecule which encodes an immunogen, and another embodiment comprises a polymeric microparticle on which a self-replicating RNA molecule which encodes an immunogen is adsorbed. In all three cases the particles preferably are substantially spherical. In a fourth embodiment a particle of the invention comprises the particulate reaction product of a polymer, a crosslinker, self-replicating RNA molecule which encodes an immunogen, and a charged monomer. These particles are formed within molds and so can be created with any shape including, but not limited to, spheres.

RNA can be encapsulated within the particles (particularly if the particle is a liposome). This means that RNA inside the particles is (as in a natural virus) separated from any external medium by the delivery material, and encapsulation has been found to protect RNA from RNase digestion. Encapsulation can take various forms. For example, in some embodiments (as in a unilamellar liposome) the delivery material forms a outer layer around an aqueous RNA-containing core, whereas in other embodiments (e.g. in molded particles) the delivery material forms a matrix within which RNA is embedded. The particles can include some external RNA (e.g. on the surface of the particles), but at least half of the RNA (and ideally all of it) is encapsulated. Encapsulation within liposomes is distinct from, for instance, the lipid/RNA complexes disclosed in reference 1.

RNA can be adsorbed to the particles (particularly if the particle is a polymeric microparticle). This means that RNA is not separated from any external medium by the delivery material, unlike the RNA genome of a natural virus. The particles can include some encapsulated RNA (e.g. in the core of a particle), but at least half of the RNA (and ideally all of it) is adsorbed.

Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic and others are cationic. Suitable classes of phospholipid include, but are not limited to, phosphatidylethanolamines, phosphatidylcholines, phosphatidylserines, and phosphatidyl-glycerols, and some useful phospholipids are listed in Table 1. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC and dodecylphosphocholine. The lipids can be saturated or unsaturated. The use of at least one unsaturated lipid for preparing liposomes is preferred. If an unsaturated lipid has two tails, both tails can be unsaturated, or it can have one saturated tail and one unsaturated tail.

Liposomal particles of the invention can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMG (anionic, saturated). Where a mixture of lipids is used, not all of the component lipids in the mixture need to be amphiphilic e.g. one or more amphiphilic lipids can be mixed with cholesterol.

The hydrophilic portion of a lipid can be PEGylated (i.e. modified by covalent attachment of a polyethylene glycol). This modification can increase stability and prevent non-specific adsorption of the liposomes. For instance, lipids can be conjugated to PEG using techniques such as those disclosed in reference 2 and 3. Various lengths of PEG can be used e.g. between 0.5-8 kDa.

A mixture of DSPC, DlinDMA, PEG-DMG and cholesterol is used in the examples.

Liposomal particles are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomal particles of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2. The liposome/RNA complexes of reference 1 are expected to have a diameter in the range of 600-800 nm and to have a high polydispersity.

Techniques for preparing suitable liposomes are well known in the art e.g. see references 4 to 6. One useful method is described in reference 7 and involves mixing (i) an ethanolic solution of the lipids (ii) an aqueous solution of the nucleic acid and (iii) buffer, followed by mixing, equilibration, dilution and purification. Preferred liposomes of the invention are obtainable by this mixing process.

Polymeric Microparticles

Various polymers can form microparticles to encapsulate or adsorb RNA according to the invention. The use of a substantially non-toxic polymer means that a recipient can safely receive the particles, and the use of a biodegradable polymer means that the particles can be metabolised after delivery to avoid long-term persistence. Useful polymers are also sterilisable, to assist in preparing pharmaceutical grade formulations.

Suitable non-toxic and biodegradable polymers include, but are not limited to, poly($\alpha$-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates or polyester-amides, and combinations thereof.

In some embodiments, the microparticles are formed from poly($\alpha$-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20 e.g. 25:75, 40:60, 45:55, 50:50, 55:45, 60:40, 75:25. Useful PLG polymers include those having a molecular weight between, for example, 5,000-200,000 Da e.g. between 10,000-100,000, 20,000-70,000, 30,000-40,000, 40,000-50,000 Da.

The microparticles ideally have a diameter in the range of 0.02 µm to 8 µm. For a composition comprising a population of microparticles with different diameters at least 80% by number should have diameters in the range of 0.03-7 µm.

Techniques for preparing suitable microparticles are well known in the art e.g. see references 6, 8 (in particular chapter 7) and 9. To facilitate adsorption of RNA, a microparticle may include a cationic surfactant and/or lipid e.g. as disclosed in references 10 & 11.

Microparticles of the invention can have a zeta potential of between 40-100 mV.

One advantage of microparticles over liposomes is that they are readily lyophilised for stable storage.

Molded Particles

A third delivery material of interest is the particulate reaction product of a polymer, a crosslinker, a self-replicating RNA which encodes an immunogen, and a charged monomer. These four components can be mixed as a liquid, placed in a mold (e.g. comprising a perfluoropolyether), and then cured to form the particles according to the mold's shape and dimensions. Details of a suitable production method are disclosed in ref. 12. These methods provide a biodegradable crosslinked oligomeric polymer nanoparticle.

Ideally the particles have a largest cross-sectional dimension of ≤5 µm. They may have an overall positive charge.

Suitable polymers include, but are not limited to: a poly(acrylic acid); a poly(styrene sulfonate); a carboxymethylcellulose (CMC); a poly(vinyl alcohol); a poly(ethylene oxide); a poly(vinyl pyrrolidone); a dextran; a poly(vinylpyrolidone-co-vinyl acetate-co-vinyl alcohol). A preferred polymer is a poly(vinyl pyrrolidinone). The amount of polymer for forming the particles can be between 2-75 wt % e.g. 10-60 wt %, 20-60 wt %.

Suitable crosslinkers can include a disulfide and/or ketal. For example, the crosslinker can comprise poly(epsilon-caprolactone)-b-tetraethylene glycol-b-poly(epsilon-caprolactone)dimethacrylate, poly(epsilon-caprolactone)-b-poly(ethylene glycol)-b-poly(epsilon-capro lactone)dimethacrylate, poly(lactic acid)-b-tetraethylene glycol-b-poly(lactic acid)dimethacrylate, poly(lactic acid)-b-poly(ethylene glycol)-b-poly(lactic acid)dimethacrylate, poly(glycolic acid)-b-tetraethylene glycol-b-poly(glycolic acid)dimethacrylate, poly(gly colic acid)-b-poly(ethylene glycol)-b-poly(gly colic acid)dimethacrylate, poly(epsilon-caprolactone)-b-tetraethylene glycol-b-poly(epsilon-caprolactone)diacrylate, poly(epsilon-caprolactone)-b-poly(ethylene glycol)-b-poly(epsilon-caprolactone)diacrylate, poly(lactic acid)-b-tetraethylene glycol-b-poly(lactic acid)diacrylate, poly(lactic acid)-b-poly(ethylene glycol)-b-poly(lactic acid)diacrylate, poly(glycolic acid)-b-tetraethylene glycol-b-poly(glycolic acid)diacrylate, poly(glycolic acid)-b-poly(ethylene glycol)-b-poly(glycolic acid)diacrylate, silane, silicon containing methacrylates, or dimethyldi(methacryloyloxy-1-ethoxy)silane. The amount of crosslinker for forming the particles can be between 10-25 wt % e.g. 10-60 wt %, 20-60 wt %.

Charged monomers can be cationic or anionic. These include, but are not limited to: [2-(acryloyloxy)ethyl]trimethyl ammonium chloride (AETMAC) and 2-aminoethyl methacrylate hydrochloride (AEM-HCl). The amount of charged monomer for forming the particles can be between 2-75 wt %.

The amount of RNA for forming the particles can be between 0.25-20 wt %.

A pre-cure mixture inside a mold can include an initiator. For instance, the mold can include ≤1 wt % initiator, ≤0.5 wt % initiator, or ≤0.1 wt % initiator. Between 0.1-0.5% initiator is useful. Photoinitiators such as DEAP and DPT are useful e.g. for use with ultraviolet curing.

The invention can use any of the materials disclosed in Table 1 or Examples 1-15 of reference 12, except that the siRNA components therein will be replaced by self-replicating RNAs as herein.

The RNA

Particles of the invention include a self-replicating RNA molecule which (unlike siRNA) encodes an immunogen. After in vivo administration of the particles, RNA is released from the particles and is translated inside a cell to provide the immunogen in situ.

Unlike reference 13, the RNA in particles of the invention is self-replicating. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall results of this sequence of transcriptions is a huge amplification in the number of the introduced replicon RNAs and so the encoded immunogen becomes a major polypeptide product of the cells.

One suitable system for achieving self-replication in this manner is to use an alphavirus-based replicon. These replicons are +-stranded RNAs which lead to translation of a replicase (or replicase-transcriptase) after delivery to a cell. The replicase is translated as a polyprotein which autocleaves to provide a replication complex which creates genomic --strand copies of the +-strand delivered RNA. These --strand transcripts can themselves be transcribed to give further copies of the +-stranded parent RNA and also to give a subgenomic transcript which encodes the immunogen. Translation of the subgenomic transcript thus leads to in situ expression of the immunogen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons [14].

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, it is preferred that the self-replicating RNA molecules of the invention do not encode alphavirus structural proteins. Thus a preferred self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an immunogen. In some embodiments the RNA may have additional (e.g. downstream) open reading frames e.g. to encode further immunogens (see below) or to encode accessory polypeptides.

A preferred self-replicating RNA molecule has a 5' cap (e.g. a 7-methylguanosine). This cap can enhance in vivo translation of the RNA. In some embodiments the 5' sequence of the self-replicating RNA molecule must be selected to ensure compatibility with the encoded replicase.

A self-replicating RNA molecule may have a 3' poly-A tail. It may also include a poly-A polymerase recognition sequence (e.g. AAUAAA) near its 3' end.

Self-replicating RNA molecules can have various lengths but they are typically 5000-25000 nucleotides long e.g. 8000-15000 nucleotides, or 9000-12000 nucleotides. Thus the RNA is longer than seen in siRNA delivery.

Self-replicating RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The self-replicating RNA can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the self-replicating RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

As discussed in reference 15, the self-replicating RNA can include (in addition to any 5' cap structure) one or more nucleotides having a modified nucleobase. Thus the RNA can comprise m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2 m6A (2-methylthio-N6-methyladenosine); i6A (N6-isopentenyladenosine); ms2i6A (2-methylthio-N6 isopentenyladenosine); io6A (N6-(cis-hydroxyisopentenyl)adenosine); ms2io6A (2-methylthio-N6-(cis-hydroxyisopentenyl)adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6.-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C(N4-acetylcytidine); f5C (5-fonnylcytidine); m5 Cm (5,2-O-dimethylcytidine); ac4 Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-β-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G (archaeosine); D (dihydrouridine); m5Um (5,2'-β-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4 Cm (N4,2-O-dimethylcytidine); hm5C (5-hydroxymethylcytidine); m3U (3-methyluridine); cm5U (5-carboxymethyluridine); m6 Am (N6,T-O-dimethyladenosine); rn62 Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5 Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide. For instance, a self-replicating RNA can include one or more modified pyrimidine nucleobases, such as pseudouridine and/or 5-methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7'-methylguanosine). In other embodiments, the RNA may include a 5' cap comprising a 7'-methylguanosine, and the first 1, 2 or 3 5' ribonucleotides may be methylated at the 2' position of the ribose.

A RNA used with the invention ideally includes only phosphodiester linkages between nucleosides, but in some embodiments it can contain phosphoramidate, phosphorothioate, and/or methylphosphonate linkages.

The amount of RNA per particle can vary, and the number of individual self-replicating RNA molecules per particle can depend on the characteristics of the particle being used. In general, a particle may include from 1-500 RNA molecules. For a liposome the number of RNA molecules is typically ≤50 per liposome e.g. <20, <10, <5, or 1-4. For a polymeric microparticle the number of RNA molecules will depend on the particle diameter but may be ≤50 per particle (e.g. <20, <10, <5, or 1-4) or from 50-200 per particle. Ideally, a particle includes fewer than 10 different species of RNA e.g. 5, 4, 3, or 2 different species; most preferably, a particle includes a single RNA species i.e. all RNA molecules in the particle have the same sequence and same length.

The Immunogen

Self-replicating RNA molecules used with the invention encode a polypeptide immunogen. After administration of the particles the immunogen is translated in vivo and can elicit an immune response in the recipient. The immunogen may elicit an immune response against a bacterium, a virus, a fungus or a parasite (or, in some embodiments, against an allergen; and in other embodiments, against a tumor antigen). The immune response may comprise an antibody response (usually including IgG) and/or a cell-mediated immune response. The polypeptide immunogen will typically elicit an immune response which recognises the corresponding bacterial, viral, fungal or parasite (or allergen or tumour) polypeptide, but in some embodiments the polypeptide may act as a mimotope to elicit an immune response which recognises a bacterial, viral, fungal or parasite saccharide. The immunogen will typically be a surface polypeptide e.g. an adhesin, a hemagglutinin, an envelope glycoprotein, a spike glycoprotein, etc.

Self-replicating RNA molecules can encode a single polypeptide immunogen or multiple polypeptides. Multiple immunogens can be presented as a single polypeptide immunogen (fusion polypeptide) or as separate polypeptides. If immunogens are expressed as separate polypeptides then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Unlike references 1 and 16, the RNA encodes an immunogen. For the avoidance of doubt, the invention does not encompass RNA which encodes a firefly luciferase or which encodes a fusion protein of *E. coli* β-galactosidase or which encodes a green fluorescent protein (GFP). Also, the RNA is not total mouse thymus RNA.

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in reference 17.

*Streptococcus pneumoniae*: useful polypeptide immunogens are disclosed in reference 18. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in references 19 and 20.

*Moraxella catarrhalis.*

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, the polypeptides disclosed in reference 21, such as a hemolysin, esxA, esxB, ferrichrome-binding protein (sta006) and/or the sta011 lipoprotein.

*Clostridium tetani*: the typical immunogen is tetanus toxoid.

*Cornynebacterium diphtheriae*: the typical immunogen is diphtheria toxoid.

*Haemophilus influenzae*: Useful immunogens include, but are not limited to, the polypeptides disclosed in references 22 and 23.

*Pseudomonas aeruginosa*

*Streptococcus agalactiae*: useful immunogens include, but are not limited to, the polypeptides disclosed in reference 19.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in reference 24. LcrE [25] and HtrA [26] are two preferred immunogens.

*Chlamydia pneumoniae*: Useful immunogens include, but are not limited to, the polypeptides disclosed in reference 27.

*Helicobacter pylori*: Useful immunogens include, but are not limited to, CagA, VacA, NAP, and/or urease [28].

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC polypeptide immunogens are disclosed in references 29 and 30. Useful MNEC immunogens are disclosed in reference 31. A useful immunogen for several *E. coli* types is AcfD [32].

*Bacillus anthracia*

*Yersinia pestis*: Useful immunogens include, but are not limited to, those disclosed in references 33 and 34.

*Staphylococcus epidermis*

*Clostridium perfringens* or *Clostridium botulinums*

*Legionella pneumophila*

*Coxiella burnetii*

*Brucella*, such as *B. abortus, B. canis, B. melitensis, B. neotomae, B. ovis, B. suis, B. pinnipediae.*

*Francisella*, such as *F. novicida, F. philomiragia, F. tularensis.*

*Neisseria gonorrhoeae*

*Treponema pallidum*

*Haemophilus ducreyi*

*Enterococcus faecalis* or *Enterococcus faecium*

*Staphylococcus saprophyticus*

*Yersinia enterocolitica*

*Mycobacterium tuberculosis*

*Rickettsia*

*Listeria monocytogenes*

*Vibrio cholerae*

*Salmonella typhi*

*Borrelia burgdorferi*

*Porphyromonas gingivalis*

*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: Viral immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles).

Poxyiridae: Viral immunogens include, but are not limited to, those derived from *Orthopoxvirus* such as Variola vera, including but not limited to, Variola major and Variola minor.

Picornavirus: Viral immunogens include, but are not limited to, those derived from Picornaviruses, such as Enteroviruses, Rhinoviruses, *Heparnavirus*, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: Viral immunogens include, but are not limited to, those derived from an *Orthobunyavirus*, such as California encephalitis virus, a *Phlebovirus*, such as Rift Valley Fever virus, or a *Nairovirus*, such as Crimean-Congo hemorrhagic fever virus.

*Heparnavirus*: Viral immunogens include, but are not limited to, those derived from a *Heparnavirus*, such as hepatitis A virus (HAV).

Filovirus: Viral immunogens include, but are not limited to, those derived from a Filovirus, such as an Ebola virus (including a Zaire, Ivory Coast, Reston or Sudan ebolavirus) or a Marburg virus.

Togavirus: Viral immunogens include, but are not limited to, those derived from a Togavirus, such as a Rubivirus, an Alphavirus, or an Arterivirus. This includes rubella virus.

*Flavivirus*: Viral immunogens include, but are not limited to, those derived from a *Flavivirus*, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St.

Louis encephalitis virus, Russian spring-summer encephalitis virus, Powassan encephalitis virus.

*Pestivirus*: Viral immunogens include, but are not limited to, those derived from a *Pestivirus*, such as Bovine viral diarrhea (BVDV), Classical swine fever (CSFV) or Border disease (BDV).

Hepadnavirus: Viral immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: Viral immunogens include, but are not limited to, those derived from a Rhabdovirus, such as a *Lyssavirus* (e.g. a Rabies virus) and Vesiculovirus (VSV).

Caliciviridae: Viral immunogens include, but are not limited to, those derived from Calciviridae, such as Norwalk virus (*Norovirus*), and Norwalk-like Viruses, such as Hawaii Virus and Snow Mountain Virus.

*Coronavirus*: Viral immunogens include, but are not limited to, those derived from a SARS *coronavirus*, avian infectious bronchitis (IBV), Mouse hepatitis virus (MHV), and Porcine transmissible gastroenteritis virus (TGEV). The coronavirus immunogen may be a spike polypeptide.

Retrovirus: Viral immunogens include, but are not limited to, those derived from an Oncovirus, a *Lentivirus* (e.g. HIV-1 or HIV-2) or a *Spumavirus*.

Reovirus: Viral immunogens include, but are not limited to, those derived from an *Orthoreovirus*, a *Rotavirus*, an *Orbivirus*, or a *Coltivirus*.

*Parvovirus*: Viral immunogens include, but are not limited to, those derived from *Parvovirus* B19.

Herpesvirus: Viral immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: Viral immunogens include those derived from adenovirus serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella* pneumoniae, *Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale*. Thus the invention may be used for immunising against malaria.

In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. Lepidoglyphys, Glycyphagus and *Tyrophagus*, those from cockroaches, midges and fleas e.g. *Blatella, Periplaneta, Chironomus* and Ctenocepphalides, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

Particles of the invention are useful as components in pharmaceutical compositions for immunising subjects against various diseases. These compositions will typically include a pharmaceutically acceptable carrier in addition to the particles. A thorough discussion of pharmaceutically acceptable carriers is available in reference 35.

A pharmaceutical composition of the invention may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Where a RNA is encapsulated, in some embodiments such agonist(s) are also encapsulated with the RNA, but in other embodiments they are unencapsulated. Where a RNA is adsorbed to a particle, in some embodiments such agonist(s) are also adsorbed with the RNA, but in other embodiments they are unadsorbed.

Pharmaceutical compositions of the invention may include the particles in plain water (e.g. w.f.i.) or in a buffer e.g. a phosphate buffer, a Tris buffer, a borate buffer, a succinate buffer, a histidine buffer, or a citrate buffer. Buffer salts will typically be included in the 5-20 mM range.

Pharmaceutical compositions of the invention may have a pH between 5.0 and 9.5 e.g. between 6.0 and 8.0.

Compositions of the invention may include sodium salts (e.g. sodium chloride) to give tonicity. A concentration of 10±2 mg/ml NaCl is typical e.g. about 9 mg/ml.

Compositions of the invention may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared.

Pharmaceutical compositions of the invention are preferably sterile.

Pharmaceutical compositions of the invention are preferably non-pyrogenic e.g. containing <1 EU (endotoxin unit, a standard measure) per dose, and preferably <0.1 EU per dose.

Pharmaceutical compositions of the invention are preferably gluten free.

Pharmaceutical compositions of the invention may be prepared in unit dose form. In some embodiments a unit dose may have a volume of between 0.1-1.0 ml e.g. about 0.5 ml.

The compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Compositions comprise an immunologically effective amount of particles, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The particle and RNA content of compositions of the invention will generally be expressed in terms of the amount of RNA per dose. A preferred dose has ≤100 μg RNA (e.g. from 10-100 μg, such as about 10 μg, 25 μg, 50 μg, 75 μg or 100 μg), but expression can be seen at much lower levels e.g. ≤1 μg/dose, ≤100 μg/dose, ≤10 μg/dose, ≤1 μg/dose, etc The invention also provides a delivery device (e.g. syringe, nebuliser, sprayer, inhaler, dermal patch, etc.) containing a pharmaceutical composition of the invention. This device can be used to administer the composition to a vertebrate subject.

Particles of the invention do not include ribosomes.

Methods of Treatment and Medical Uses

In contrast to the particles disclosed in reference 16, particles and pharmaceutical compositions of the invention are for in vivo use for eliciting an immune response against an immunogen of interest.

The invention provides a method for raising an immune response in a vertebrate comprising the step of administering an effective amount of a particle or pharmaceutical composition of the invention. The immune response is preferably protective and preferably involves antibodies and/or cell-mediated immunity. The method may raise a booster response.

The invention also provides a particle or pharmaceutical composition of the invention for use in a method for raising an immune response in a vertebrate.

The invention also provides the use of a particle of the invention in the manufacture of a medicament for raising an immune response in a vertebrate.

By raising an immune response in the vertebrate by these uses and methods, the vertebrate can be protected against various diseases and/or infections e.g. against bacterial and/or viral diseases as discussed above. The particles and compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; unlike reference 1, intraglossal injection is not typically used with the present invention). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to elicit systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

GENERAL EMBODIMENTS

In some embodiments of the invention, the RNA includes no modified nucleotides (see above). In other embodiments the RNA can optionally include at least one modified nucleotide, provided that one or more of the following features (already disclosed above) is also required:

A. Where the RNA is delivered with a liposome, the liposome comprises DSDMA, DODMA, DLinDMA and/or DLenDMA.

B. Where the RNA is encapsulated in a liposome, the hydrophilic portion of a lipid in the liposome is PEGylated.

C. Where the RNA is encapsulated in a liposome, at least 80% by number of the liposomes have diameters in the range of 20-220 nm.

D. Where the RNA is delivered with a microparticle, the microparticle is a non-toxic and biodegradable polymer microparticle.

E. Where the RNA is delivered with a microparticle, the microparticles have a diameter in the range of 0.02 μm to 8 μm.

F. Where the RNA is delivered with a microparticle, at least 80% by number of the microparticles have a diameter in the range of 0.03-7 μm.

G. Where the RNA is delivered with a microparticle, the composition is lyophilised.

H. The RNA has a 3' poly-A tail, and the immunogen can elicits an immune response in vivo against a bacterium, a virus, a fungus or a parasite.

I. The RNA is delivered in combination with a metal ion chelator with a delivery system selected from (i) liposomes (ii) non-toxic and biodegradable polymer microparticles.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 36-42, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to charge, to cations, to anions, to zwitterions, etc., are taken at pH 7.

TLR3 is the Toll-like receptor 3. It is a single membrane-spanning receptor which plays a key role in the innate immune system. Known TLR3 agonists include poly(I:C). "TLR3" is the approved HGNC name for the gene encoding this receptor, and its unique HGNC ID is HGNC:11849. The RefSeq sequence for the human TLR3 gene is GI:2459625.

TLR7 is the Toll-like receptor 7. It is a single membrane-spanning receptor which plays a key role in the innate immune system. Known TLR7 agonists include e.g. imiquimod. "TLR7" is the approved HGNC name for the gene encoding this receptor, and its unique HGNC ID is HGNC:15631. The RefSeq sequence for the human TLR7 gene is GI:67944638.

TLR8 is the Toll-like receptor 8. It is a single membrane-spanning receptor which plays a key role in the innate immune system. Known TLR8 agonists include e.g. resiquimod. "TLR8" is the approved HGNC name for the gene encoding this receptor, and its unique HGNC ID is HGNC:15632. The RefSeq sequence for the human TLR8 gene is GI:20302165.

The RIG-I-like receptor ("RLR") family includes various RNA helicases which play key roles in the innate immune system[43]. RLR-1 (also known as RIG-I or retinoic acid inducible gene I) has two caspase recruitment domains near its N-terminus. The approved HGNC name for the gene encoding the RLR-1 helicase is "DDX58" (for DEAD (Asp-Glu-Ala-Asp) box polypeptide 58) and the unique HGNC ID is HGNC:19102. The RefSeq sequence for the human RLR-1 gene is GI:77732514. RLR-2 (also known as MDA5 or melanoma differentiation-associated gene 5) also has two caspase recruitment domains near its N-terminus. The approved HGNC name for the gene encoding the RLR-2 helicase is "IFIH1" (for interferon induced with helicase C domain 1) and the unique HGNC ID is HGNC:18873. The RefSeq sequence for the human RLR-2 gene is GI: 27886567. RLR-3 (also known as LGP2 or laboratory of genetics and physiology 2) has no caspase recruitment domains. The approved HGNC name for the gene encoding the RLR-3 helicase is "DHX58" (for DEXH (Asp-Glu-X-His) box polypeptide 58) and the unique HGNC ID is HGNC:29517. The RefSeq sequence for the human RLR-3 gene is GI:149408121.

PKR is a double-stranded RNA-dependent protein kinase. It plays a key role in the innate immune system. "EIF2AK2" (for eukaryotic translation initiation factor 2-alpha kinase 2) is the approved HGNC name for the gene encoding this enzyme, and its unique HGNC ID is HGNC:9437. The RefSeq sequence for the human PKR gene is GI:208431825.

BRIEF DESCRIPTION OF DRAWINGS

FIG. 13 shows intracellular cytokine production after restimulation with synthetic peptides representing the major epitopes in the F protein, 4 weeks after a second dose. The y-axis shows the % cytokine+ of CD8+CD4−.

FIG. 17 shows (A) IL-6 and (B) IFNα (pg/ml) released by pDC. There are 4 pairs of bars, from left to right: control; immunised with RNA+DOTAP; immunised with RNA+ lipofectamine; and immunised with RNA in liposomes. In each pair the black bar is wild-type mice, grey is rsq1 mutant.

MODES FOR CARRYING OUT THE INVENTION

RNA Replicons

Figure 1:
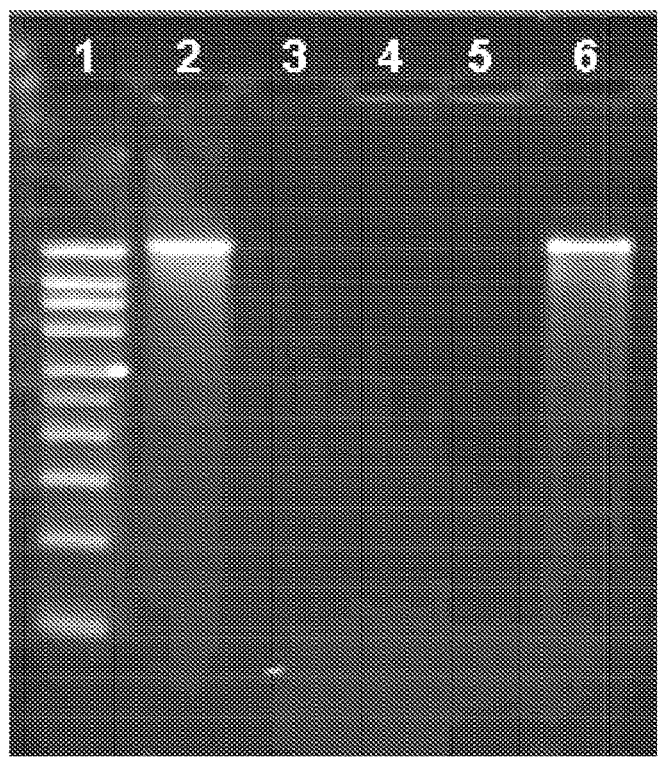
FIG. 1 shows a gel with stained RNA. Lanes show (1) markers (2) naked replicon (3) replicon after RNase treatment (4) replicon encapsulated in liposome (5) liposome after RNase treatment (6) liposome treated with RNase then subjected to phenol/chloroform extraction.

Various replicons are used below. In general these are based on a hybrid alphavirus genome with non-structural proteins from venezuelan equine encephalitis virus (VEEV), a packaging signal from sindbis virus, and a 3' UTR from Sindbis virus or a VEEV mutant. The replicon is about 10 kb long and has a poly-A tail.

Plasmid DNA encoding alphavirus replicons (named: pT7-mVEEV-FL.RSVF or A317; pT7-mVEEV-SEAP or A306; pSP6-VCR-GFP or A50) served as a template for synthesis of RNA in vitro. The replicons contain the alphavirus genetic elements required for RNA replication but lack those encoding gene products necessary for particle assembly; the structural proteins are instead replaced by a protein of interest (either a reporter, such as SEAP or GFP, or an immunogen, such as full-length RSV F protein) and so the replicons are incapable of inducing the generation of infectious particles. A bacteriophage (T7 or SP6) promoter upstream of the alphavirus cDNA facilitates the synthesis of the replicon RNA in vitro and a hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion). Following transcription the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of the RNA samples was determined by measuring $OD_{260nm}$. Integrity of the in vitro transcripts was confirmed by denaturing agarose gel electrophoresis.

PLG Adsorption

Microparticles were made using 500 mg of PLG RG503 (50:50 lactide/glycolide molar ratio, MW ~30 kDa) and 20 mg DOTAP using an Omni Macro Homogenizer. The particle suspension was shaken at 150 rpm overnight and then filtered through a 40 μm sterile filter for storage at 2-8° C. Self-replicating RNA was adsorbed to the particles. To prepare 1 mL of PLG/RNA suspension the required volume of PLG particle suspension was added to a vial and nuclease-free water was added to bring the volume to 900 μL. 100 μL RNA (10 μg/mL) was added dropwise to the PLG suspension, with constant shaking. PLG/RNA was incubated at room temperature for 30 min. For 1 mL of reconstituted suspension, 45 mg mannitol, 15 mg sucrose and 250-500 μg of PVA were added. The vials were frozen at −80° C. and lyophilized.

To evaluate RNA adsorption, 100 μL particle suspension was centrifuged at 10,000 rpm for 5 min and supernatant was collected. PLG/RNA was reconstituted using 1 mL nuclease-free water. To 100 μL particle suspension (1 μg RNA), 1 mg heparin sulfate was added. The mixture was vortexed and allowed to sit at room temperature for 30 min for RNA desorption. Particle suspension was centrifuged and supernatant was collected.

For RNAse stability, 100 μL particle suspension was incubated with 6.4 mAU of RNase A at room temperature for 30 min. RNAse was inactivated with 0.126 mAU of Proteinase K at 55° C. for 10 min. 1 mg of heparin sulfate was added to desorb the RNA followed by centrifugation. The supernatant samples containing RNA were mixed with formaldehyde load dye, heated at 65° C. for 10 min and analyzed using a 1% denaturing gel (460 ng RNA loaded per lane).

Figure 3:
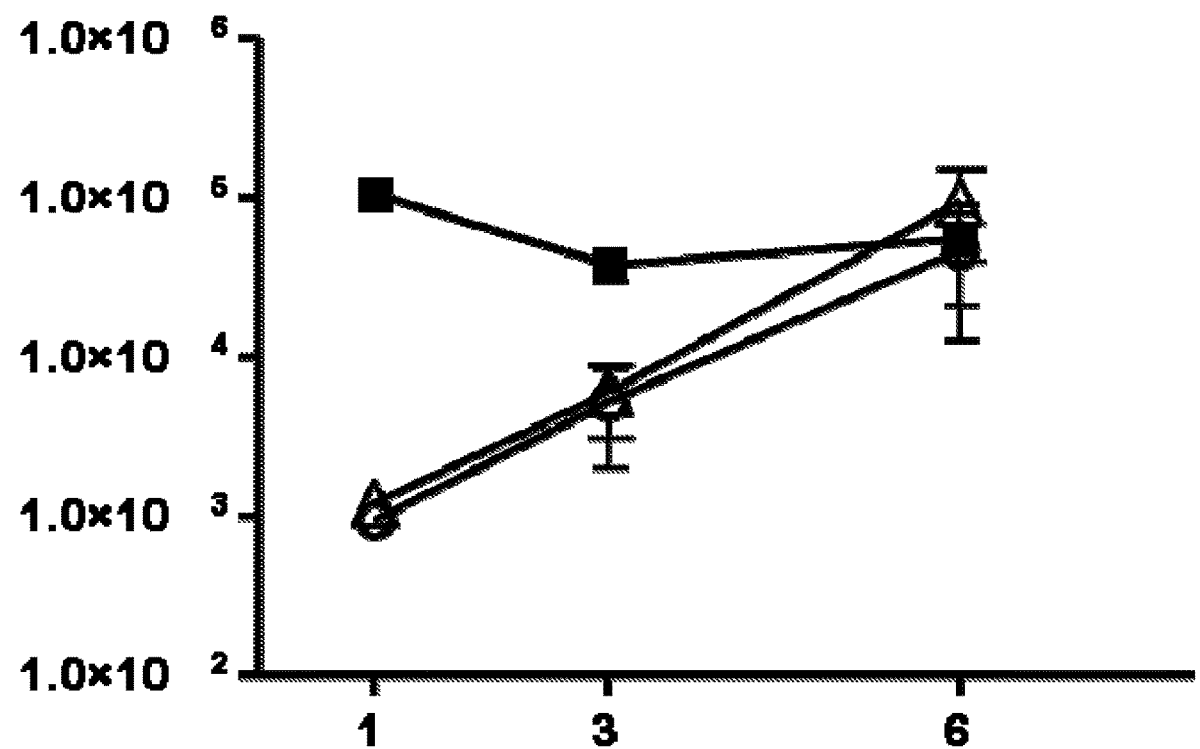
FIG. 3 shows protein expression (as relative light units, RLU) at days 1, 3 and 6 after delivery of RNA as a virion-packaged replicon (squares), naked RNA (triangles), or as microparticles (circles).

To assess expression, Balb/c mice were immunized with 1 μg RNA in 100 μL intramuscular injection volume (50 μL/leg) on day 0. Sera were collected on days 1, 3 and 6. Protein expression was determined using a chemiluminescence assay. As shown in FIG. 3, expression was higher when RNA was delivered by PLG (triangles) than without any delivery particle (circles).

Liposomal Encapsulation

RNA was encapsulated in liposomes made by the method of references 7 and 44. The liposomes were made of 10% DSPC (zwitterionic), 40% DlinDMA (cationic), 48% cholesterol and 2% PEG-conjugated DMG (2 kDa PEG). These proportions refer to the % moles in the total liposome.

DlinDMA (1,2-dilinoleyloxy-N,N-dimethyl-3-aminopropane) was synthesized using the procedure of reference 2. DSPC (1,2-Diastearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3β-[N—(N',N'-dimethylaminoethane)-carbamoyl]cholesterol hydrochloride) were from Avanti Polar Lipids.

Briefly, lipids were dissolved in ethanol (2 ml), a RNA replicon was dissolved in buffer (2 ml, 100 mM sodium citrate, pH 6) and these were mixed with 2 ml of buffer followed by 1 hour of equilibration. The mixture was diluted with 6 ml buffer then filtered. The resulting product contained liposomes, with ~95% encapsulation efficiency.

For example, in one particular method, fresh lipid stock solutions were prepared in ethanol. 37 mg of DlinDMA, 11.8 mg of DSPC, 27.8 mg of cholesterol and 8.07 mg of PEG-DMG were weighed and dissolved in 7.55 mL of ethanol. The freshly prepared lipid stock solution was gently rocked at 37° C. for about 15 min to form a homogenous mixture. Then, 755 μL of the stock was added to 1.245 mL ethanol to make a working lipid stock solution of 2 mL. This amount of lipids was used to form liposomes with 250 μg RNA. A 2 mL working solution of RNA was also prepared from a stock solution of ~1 μg/μL in 100 mM citrate buffer (pH 6). Three 20 mL glass vials (with stir bars) were rinsed with RNase Away solution (Molecular BioProducts) and washed with plenty of MilliQ water before use to decontaminate the vials of RNases. One of the vials was used for the RNA working solution and the others for collecting the lipid and RNA solutions (as described later). The working lipid and RNA solutions were heated at 37° C. for 10 min before being loaded into 3 cc luer-lok syringes. 2 mL citrate buffer (pH 6) was loaded in another 3 cc syringe. Syringes containing RNA and the lipids were connected to a T mixer (PEEK™ 500 μm ID junction, Idex Health Science) using FEP tubing (fluorinated ethylene-propylene; all FEP tubing used had a 2 mm internal diameter and a 3 mm outer diameter; obtained from Idex Health Science). The outlet from the T mixer was also FEP tubing. The third syringe containing the citrate buffer was connected to a separate piece of tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 h. 4 ml of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation). Before using this membrane for the liposomes, 4 mL of 1 M NaOH, 4 mL of 1 M NaCl and 10 mL of 100 mM citrate buffer (pH 6) were successively passed through it. Liposomes were warmed for 10 min at 37° C. before passing through the membrane. Next, liposomes were concentrated to 2 mL and dialyzed against 10-15 volumes of 1×PBS using by tangential flow filtration before recovering the final product. The TFF system and hollow fiber filtration membranes were purchased from Spectrum Labs (Rancho Dominguez) and were used according to the manufacturer's guidelines. Polysulfone hollow fiber filtration membranes with a 100 kD pore size cutoff and 8 cm² surface area were used. For in vitro and in vivo experiments formulations were diluted to the required RNA concentration with 1×PBS. Further liposome manufacturing methods are disclosed below.

Figure 2:
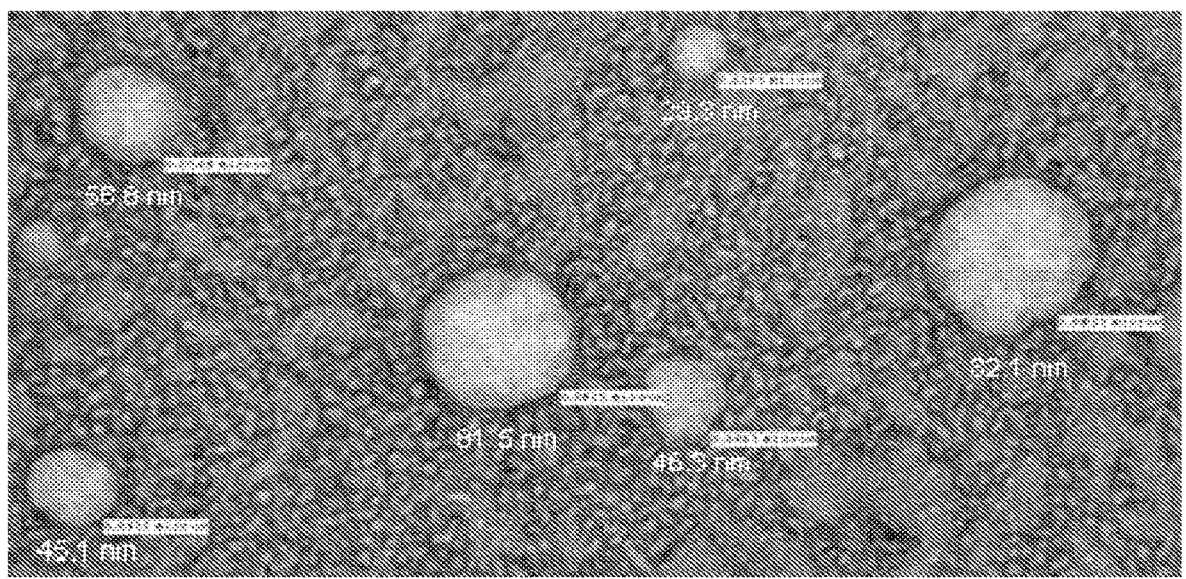
FIG. 2 is an electron micrograph of liposomes.

FIG. 2 shows an example electron micrograph of liposomes prepared by these methods. These liposomes contain encapsulated RNA encoding full-length RSV F antigen. Dynamic light scattering of one batch showed an average diameter of 141 nm (by intensity) or 78 nm (by number).

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. Liposomes were diluted 10× or 100× in 1×TE buffer (from kit) before addition of the dye. Separately, liposomes were diluted 10× or 100× in 1×TE buffer containing 0.5% Triton X before addition of the dye (to disrupt the liposomes and thus to assay total RNA). Thereafter an equal amount of dye was added to each solution and then ~180 μL of each solution after dye addition was loaded in duplicate into a 96 well tissue culture plate. The fluorescence (Ex 485 nm, Em 528 nm) was read on a microplate reader. All liposome formulations were dosed in vivo based on the encapsulated amount of RNA.

Encapsulation in liposomes was shown to protect RNA from RNase digestion. Experiments used 3.8 mAU of RNase A per microgram of RNA, incubated for 30 minutes at room temperature. RNase was inactivated with Proteinase K at 55° C. for 10 minutes. A 1:1 v/v mixture of sample to 25:24:1 v/v/v, phenol:chloroform:isoamyl alcohol was then added to extract the RNA from the lipids into the aqueous phase. Samples were mixed by vortexing for a few seconds and then placed on a centrifuge for 15 minutes at 12 k RPM. The aqueous phase (containing the RNA) was removed and used to analyze the RNA. Prior to loading (400 ng RNA per well) all the samples were incubated with formaldehyde loading dye, denatured for 10 minutes at 65° C. and cooled to room temperature. Ambion Millennium markers were used to approximate the molecular weight of the RNA construct. The gel was run at 90 V. The gel was stained using 0.1% SYBR gold according to the manufacturer's guidelines in water by rocking at room temperature for 1 hour. FIG. 1 shows that RNase completely digests RNA in the absence of encapsulation (lane 3). RNA is undetectable after encapsulation (lane 4), and no change is seen if these liposomes are treated with RNase (lane 4). After RNase-treated liposomes are subjected to phenol extraction, undigested RNA is seen (lane 6).

Figure 4:
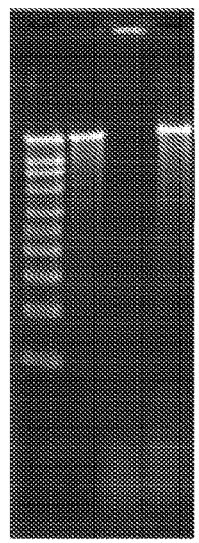
FIG. 4 shows a gel with stained RNA. Lanes show (1) markers (2) naked replicon (3) replicon encapsulated in liposome (4) liposome treated with RNase then subjected to phenol/chloroform extraction.

Even after 1 week at 4° C. the RNA could be seen without any fragmentation (FIG. 4, arrow). Protein expression in vivo was unchanged after 6 weeks at 4° C. and one freeze-thaw cycle. Thus liposome-encapsulated RNA is stable.

To assess in vivo expression of the RNA a reporter enzyme (SEAP; secreted alkaline phosphatase) was encoded in the replicon, rather than an immunogen. Expression levels were measured in sera diluted 1:4 in 1× Phospha-Light dilution buffer using a chemiluminescent alkaline phosphate substrate. 8-10 week old BALB/c mice (5/group) were injected intramuscularly on day 0, 50 μl per leg with 0.1 μg or 1 μg RNA dose. The same vector was also administered without the liposomes (in RNase free 1×PBS) at 1 μg. Virion-packaged replicons were also tested. Virion-packaged replicons used herein (referred to as "VRPs") were obtained by the methods of reference 45, where the alphavirus replicon is derived from the mutant VEEV or a chimera derived from the genome of VEEV engineered to contain the 3' UTR of Sindbis virus and a Sindbis virus packaging signal (PS), packaged by co-electroporating them into BHK cells with defective helper RNAs encoding the Sindbis virus capsid and glycoprotein genes.

Figure 5:
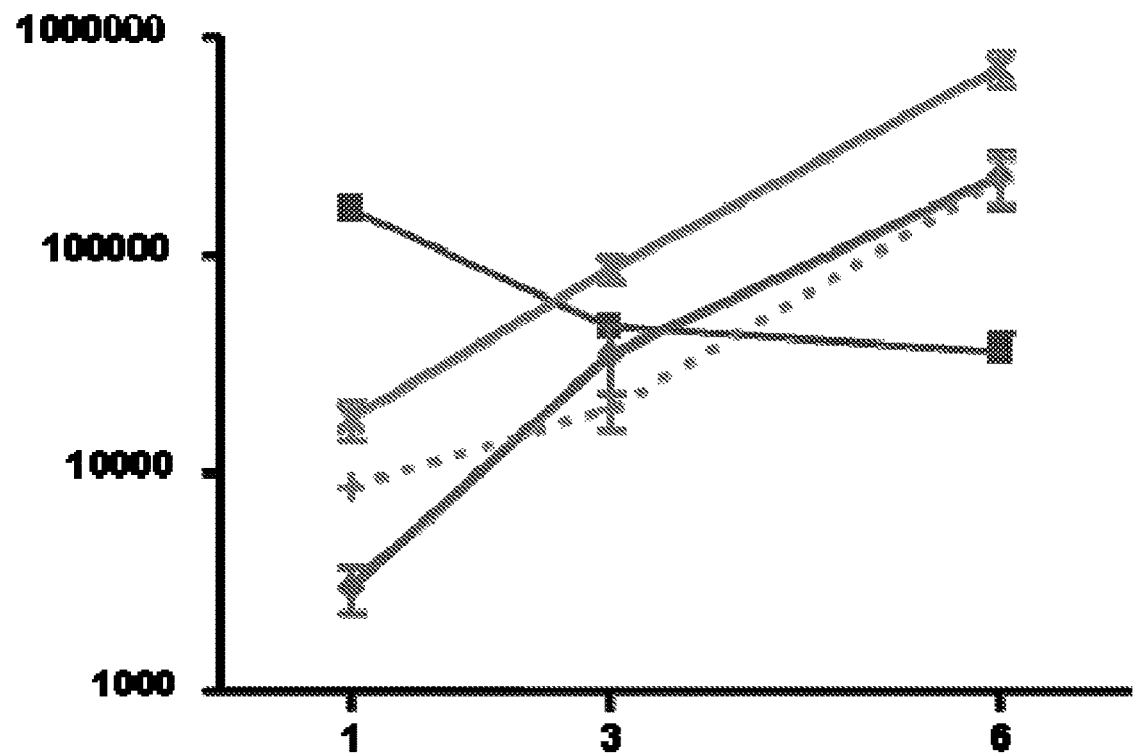
FIG. 5 shows protein expression at days 1, 3 and 6 after delivery of RNA as a virion-packaged replicon (squares), as naked RNA (diamonds), or in liposomes (+=0.1 µg, x=1 µg).

As shown in FIG. 5, encapsulation increased SEAP levels by about ½ log at the 1 μg dose, and at day 6 expression from a 0.1 μg encapsulated dose matched levels seen with 1 μg unencapsulated dose. By day 3 expression levels exceeded those achieved with VRPs (squares). Thus expressed increased when the RNA was formulated in the liposomes relative to the naked RNA control, even at a 10× lower dose. Expression was also higher relative to the VRP control, but the kinetics of expression were very different (see FIG. 5). Delivery of the RNA with electroporation resulted in increased expression relative to the naked RNA control, but these levels were lower than with liposomes.

Figure 6:
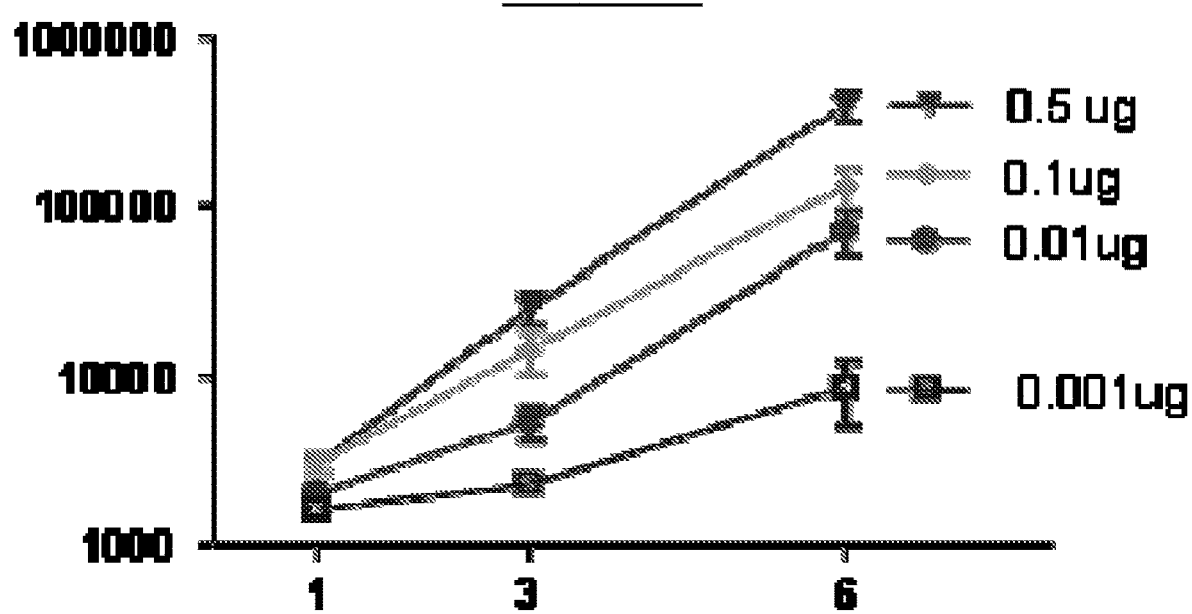
FIG. 6 shows protein expression at days 1, 3 and 6 after delivery of four different doses of liposome-encapsulated RNA.

Further SEAP experiments showed a clear dose response in vivo, with expression seen after delivery of as little as 1 ng RNA (FIG. 6). Further experiments comparing expression from encapsulated and naked replicons indicated that 0.01 μg encapsulated RNA was equivalent to 1 μg of naked RNA. At a 0.5 μg dose of RNA the encapsulated material gave a 12-fold higher expression at day 6; at a 0.1 μg dose levels were 24-fold higher at day 6.

Rather than looking at average levels in the group, individual animals were also studied. Whereas several animals were non-responders to naked replicons, encapsulation eliminated non-responders.

Further experiments replaced DlinDMA with DOTAP. Although the DOTAP liposomes gave better expression than naked replicon, they were inferior to the DlinDMA liposomes (2- to 3-fold difference at day 1).

Figure 7:
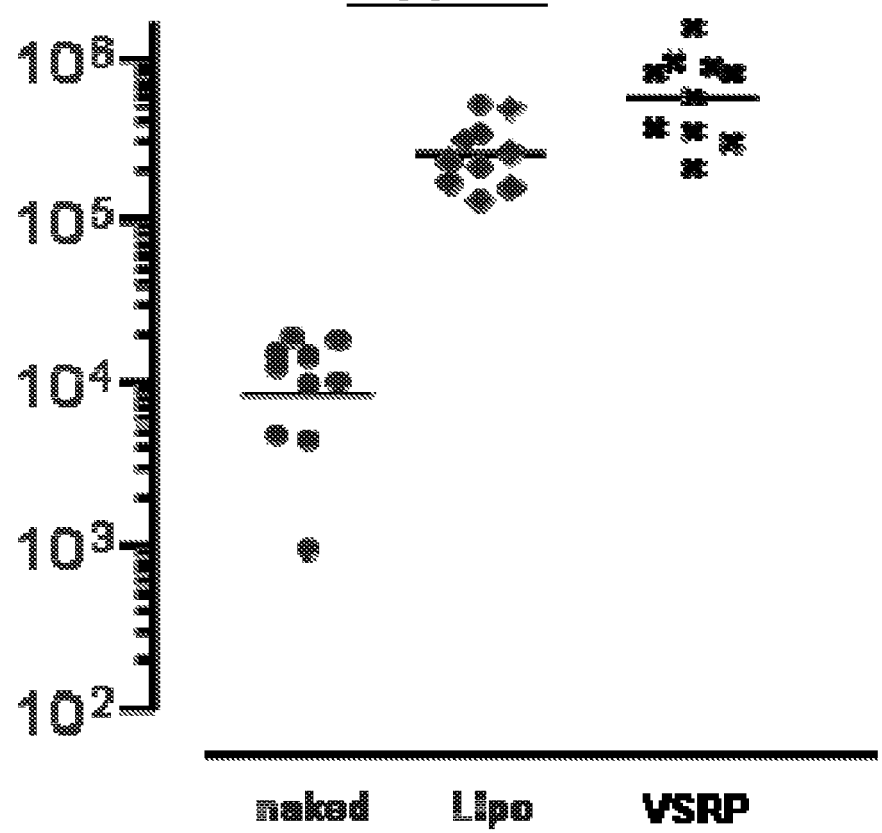
FIG. 7 shows anti-F IgG titers in animals receiving virion-packaged replicon (VRP or VSRP), 1 µg naked RNA, and 1 µg liposome-encapsulated RNA.
Figure 8:
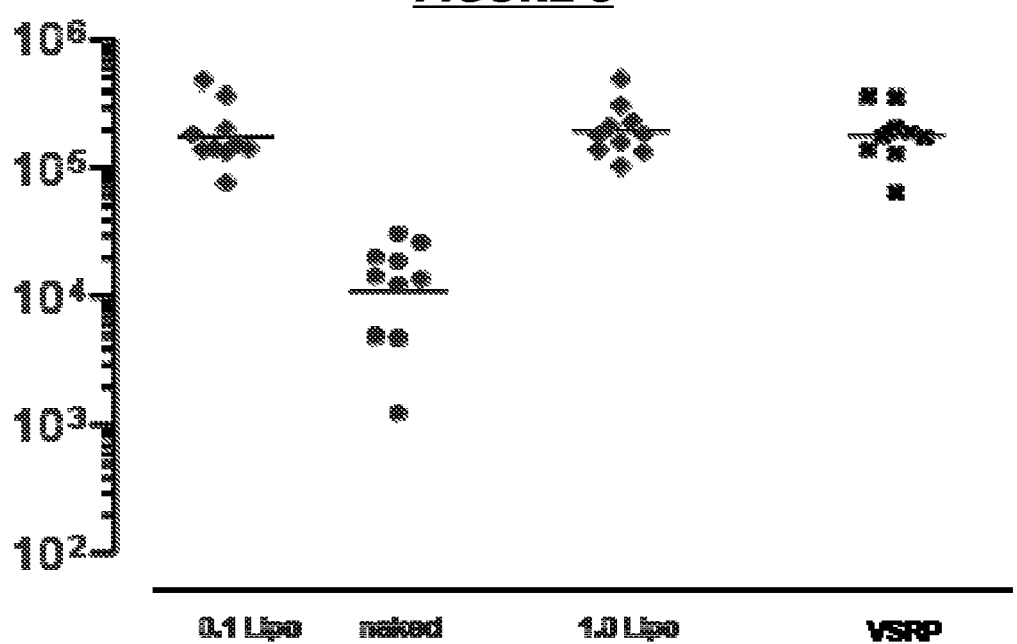
FIG. 8 shows anti-F IgG titers in animals receiving VRP, 1 µg naked RNA, and 0.1 g or 1 µg liposome-encapsulated RNA.
Figure 9:
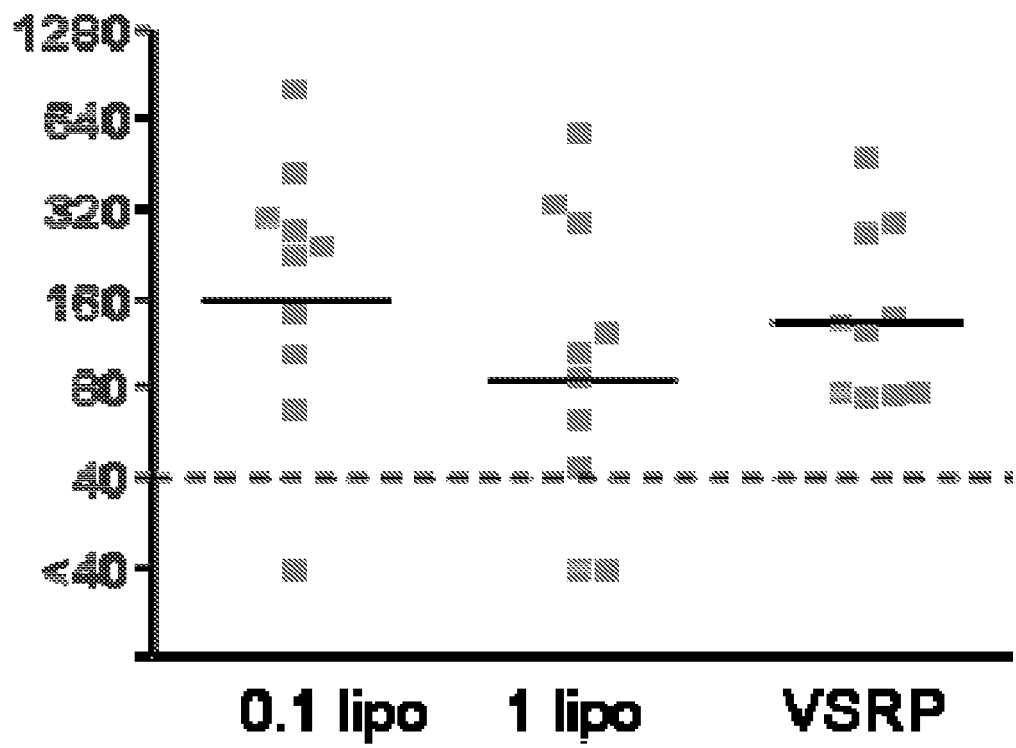
FIG. 9 shows neutralising antibody titers in animals receiving VRP or either 0.1 g or 1 µg liposome-encapsulated RNA.
Figure 12:
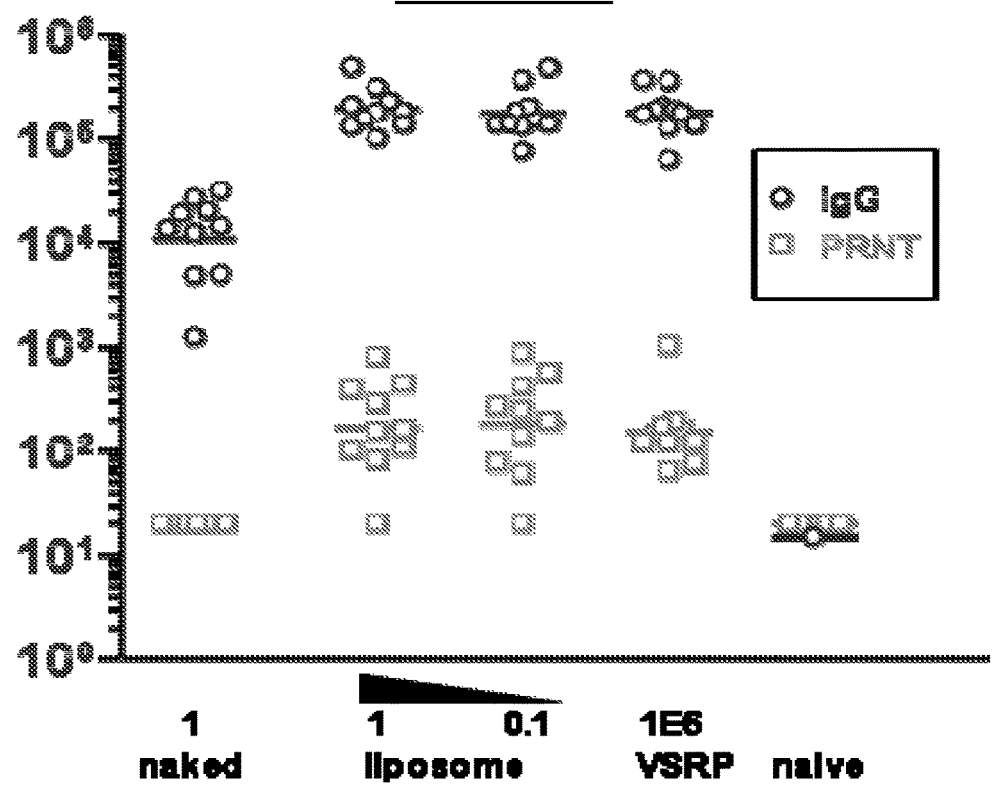
FIG. 12 shows F-specific IgG titers (circles) and PRNT titers (squares) after delivery of a replicon as naked RNA (1 µg), liposome-encapsulated RNA (0.1 or 1 µg), or packaged as a virion (VRP, $10^6$ IU). Titers in naïve mice are also shown. Solid lines show geometric means.

To assess in vivo immunogenicity a replicon was constructed to express full-length F protein from respiratory syncytial virus (RSV). This was delivered naked (1 µg), encapsulated in liposomes (0.1 or 1 µg), or packaged in virions ($10^6$ IU; "VRP") at days 0 and 21. FIG. 7 shows anti-F IgG titers 2 weeks after the second dose, and the liposomes clearly enhance immunogenicity. FIG. 8 shows titers 2 weeks later, by which point there was no statistical difference between the encapsulated RNA at 0.1 µg, the encapsulated RNA at 1 µg, or the VRP group. Neutralisation titers (measured as 60% plaque reduction, "PRNT60") were not significantly different in these three groups 2 weeks after the second dose (FIG. 9). FIG. 12 shows both IgG and PRNT titers 4 weeks after the second dose.

FIG. 13 confirms that the RNA elicits a robust CD8 T cell response.

Further experiments compared F-specific IgG titers in mice receiving VRP, 0.1 µg liposome-encapsulated RNA, or 1 µg liposome-encapsulated RNA. Titer ratios (VRP: liposome) at various times after the second dose were as follows:

|        | 2 weeks | 4 weeks | 8 weeks |
|--------|---------|---------|---------|
| 0.1 µg | 2.9     | 1.0     | 1.1     |
| 1 µg   | 2.3     | 0.9     | 0.9     |

Thus the liposome-encapsulated RNA induces essentially the same magnitude of immune response as seen with virion delivery.

Figure 11:
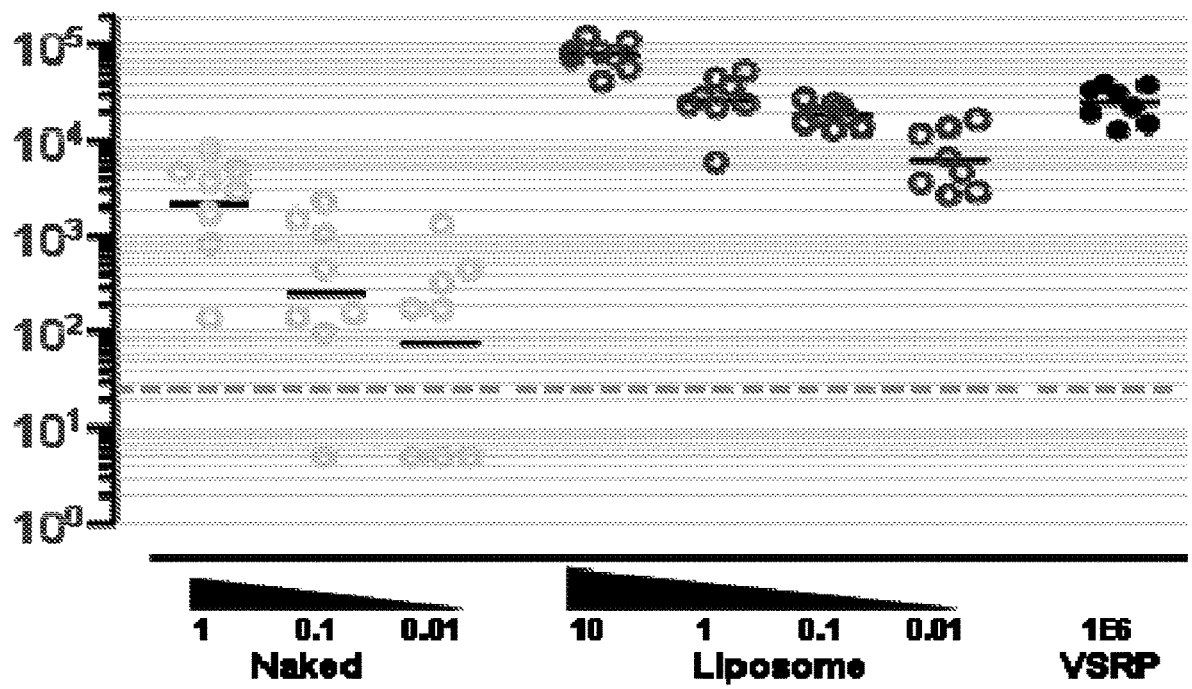
FIG. 11 shows F-specific IgG titers (2 weeks after second dose) after delivery of a replicon as naked RNA (0.01-1 µg), liposome-encapsulated RNA (0.01-10 µg), or packaged as a virion (VRP, $10^6$ infectious units or IU).

Further experiments showed superior F-specific IgG responses with a 10 µg dose, equivalent responses for 1 µg and 0.1 µg doses, and a lower response with a 0.01 µg dose. FIG. 11 shows IgG titers in mice receiving the replicon in naked form at 3 different doses, in liposomes at 4 different doses, or as VRP ($10^6$ IU). The response seen with 1 µg liposome-encapsulated RNA was statistically insignificant (ANOVA) when compared to VRP, but the higher response seen with 10 µg liposome-encapsulated RNA was statistically significant ($p<0.05$) when compared to both of these groups.

A further study confirmed that the 0.1 µg of liposome-encapsulated RNA gave much higher anti-F IgG responses (15 days post-second dose) than 0.1 µg of delivered DNA, and even was more immunogenic than 20 µg plasmid DNA encoding the F antigen, delivered by electroporation (Elgen™ DNA Delivery System, Inovio).

Mice showed few visual signs of distress (weight loss, etc.) after receiving liposome-encapsulated RNA replicon, although a transient weight loss of 3-4% was seen after a second dose of 10 µg RNA. In contrast, delivery of 10 µg liposome-encapsulated DNA led to 8-10% weight loss.

Mechanism of Action

Bone marrow derived dendritic cells (pDC) were obtained from wild-type mice or the "Resq" (rsq1) mutant strain. The mutant strain has a point mutation at the amino terminus of its TLR7 receptor which abolishes TLR7 signalling without affecting ligand binding [46]. The cells were stimulated with replicon RNA formulated with DOTAP, lipofectamine 2000 or inside a liposome. As shown in FIG. 17, IL-6 and INFα were induced in WT cells but this response was almost completely abrogated in mutant mice. These results shows that TLR7 is required for RNA recognition in immune cells, and that liposome-encapsulated replicons can cause immune cells to secrete high levels of both interferons and pro-inflammatory cytokines.

In general, liposome-delivered RNA replicons were shown to induce several serum cytokines within 24 hours of intramuscular injection (IFN-α, IP-10 (CXCL-10), IL-6, KC, IL-5, IL-13, MCP-1, and MIP-a), whereas only MIP-1 was induced by naked RNA and liposome alone induced only IL-6.

IFN-α was shown to contribute to the immune response to liposome-encapsulated RSV-F-encoding replicon because an anti-IFNα receptor (IFNAR1) antibody reduced F-specific serum IgG a 10-fold reduction after 2 vaccinations.

Liposome-delivered RNA replicons have generally been seen to elicit a balanced IgG1:IgG2a subtype profile in mice, sometimes with a higher IgG2a/IgG1 ratio than seen with electroporated DNA or with protein/MF59 immunizations (i.e. a Th1-type immune response).

Liposome Manufacturing Methods

In general, eight different methods have been used for preparing liposomes according to the invention. These are referred to in the text as methods (A) to (H) and they differ mainly in relation to filtration and TFF steps. Details are as follows:

(A) Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 min to form a homogenous mixture. Then, 755 µL of the stock was added to 1.245 mL ethanol to make a working lipid stock solution of 2 mL. This amount of lipids was used to form liposomes with 250 µg RNA. A 2 mL working solution of RNA was also prepared from a stock solution of ~1 µg/µL in 100 mM citrate buffer (pH 6). Three 20 mL glass vials (with stir bars) were rinsed with RNase Away solution (Molecular BioProducts, San Diego, Calif.) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3 cc luer-lok syringes. 2 mL of citrate buffer (pH 6) was loaded in another 3 cc syringe. Syringes containing RNA and the lipids were connected to a T mixer (PEEK™ 500 µm ID junction, Idex Health Science, Oak Harbor, Wash.) using FEP tubing (fluorinated ethylene-propylene; al FEP tubing has a 2 mm internal diameter×3 mm outer diameter, supplied by Idex Health Science). The outlet from the T mixer was also FEP tubing. The third syringe containing the citrate buffer was connected to a separate piece of FEP tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 hour. 4 ml of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation, AnnArbor, Mich., USA). Before passing the liposomes, 4 mL of 1 M NaOH, 4 mL of 1 M NaCl and 10 mL of 100 mM citrate buffer (pH 6) were successively passed through the Mustang membrane. Liposomes were warmed for 10 min at 37° C. before passing through the membrane. Next, liposomes were concentrated to 2 mL and dialyzed against 10-15 volumes of 1×PBS using TFF before recovering the final product. The TFF system and hollow fiber filtration membranes were purchased from Spectrum Labs and were used according to the manufacturer's guidelines. Polysulfone hollow fiber filtration membranes (part number P/N: X1AB-100-20P) with a 100 kD pore size cutoff and 8 cm$^2$ surface area were used. For in vitro and in vivo experiments, formulations were diluted to the required RNA concentration with 1×PBS.

(B) As method (A) except that, after rocking, 226.7 µL of the stock was added to 1.773 mL ethanol to make a working lipid stock solution of 2 mL, thus modifying the lipid:RNA ratio.

(C) As method (B) except that the Mustang filtration was omitted, so liposomes went from the 20 mL glass vial into the TFF dialysis.

(D) As method (C) except that the TFF used polyethersulfone (PES) hollow fiber membranes (part number P-C1-100E-100-01N) with a 100 kD pore size cutoff and 20 cm$^2$ surface area.

(E) As method (D) except that a Mustang membrane was used, as in method (A).

(F) As method (A) except that the Mustang filtration was omitted, so liposomes went from the 20 mL glass vial into the TFF dialysis.

(G) As method (D) except that a 4 mL working solution of RNA was prepared from a stock solution of ~1 µg/µL in 100 mM citrate buffer (pH 6). Then four 20 mL glass vials were prepared in the same way. Two of them were used for the RNA working solution (2 mL in each vial) and the others for collecting the lipid and RNA mixes, as in (C). Rather than use T mixer, syringes containing RNA and the lipids were connected to a Mitos Droplet junction Chip (a glass microfluidic device obtained from Syrris, Part no. 3000158) using PTFE tubing (0.03 inches internal diameter×1/16 inch outer diameter) using a 4-way edge connector (Syrris). Two RNA streams and one lipid stream were driven by syringe pumps and the mixing of the ethanol and aqueous phase was done at the X junction (100 µm×105 µm) of the chip. The flow rate of all three streams was kept at 1.5 mL/min, hence the ratio of total aqueous to ethanolic flow rate was 2:1. The tube outlet was positioned to collect the mixtures in a 20 mL glass vial (while stirring). The stir bar was taken out and the ethanol/aqueous solution was allowed to equilibrate to room temperature for 1 h. Then the mixture was loaded in a 5 cc syringe, which was fitted to another piece of the PTFE tubing; in another 5 cc syringe with equal length of PTFE tubing, an equal volume of 100 mM citrate buffer (pH 6) was loaded. The two syringes were driven at 3 mL/min flow rate using a syringe pump and the final mixture collected in a 20 mL glass vial (while stirring). Next, liposomes were concentrated to 2 mL and dialyzed against 10-15 volumes of 1×PBS using TFF, as in (D).

(H) As method (A) except that the 2 mL working lipid stock solution was made by mixing 120.9 µL of the lipid stock with 1.879 mL ethanol. Also, after mixing in the T mixer the liposomes from the 20 mL vial were loaded into Pierce Slide-A-Lyzer Dialysis Cassette (Thermo Scientific, extra strength, 0.5-3 mL capacity) and dialyzed against 400-500 mL of 1×PBS overnight at 4° C. in an autoclaved plastic container before recovering the final product.

BHK Expression

Liposomes with different lipids were incubated with BHK cells overnight and assessed for protein expression potency. From a baseline with RV05 lipid expression could be increased 18× by adding 10% 1,2-diphytanoyl-sn-glycero-3-phosphoethanolamine (DPyPE) to the liposome, 10× by adding 10% 18:2 (cis) phosphatidylcholine, and 900× by instead using RV01.

In general, in vivo studies showed that unsaturated lipid tails tend to enhance IgG titers raised against encoded antigens.

RSV Immunogenicity

The vA317 self-replicating replicon encoding RSV F protein was administered to BALB/c mice, 4 or 8 animals per group, by bilateral intramuscular vaccinations (50 µL per leg) on days 0 and 21 with the replicon (1 µg) alone or formulated as liposomes with DlinDMA ("RV01") or DOTAP ("RV13"). The RV01 liposomes had 40% DlinDMA, 10% DSPC, 48% cholesterol and 2% PEG-DMG, but with differing amounts of RNA. The RV13 liposomes had 40% DOTAP, 10% DPE, 48% cholesterol and 2% PEG-DMG. For comparison, naked plasmid DNA (20 µg) expressing the same RSV-F antigen was delivered either using electroporation or with RV01(10) liposomes (0.1 µg DNA). Four mice were used as a naïve control group.

Liposomes were prepared by method (D) or method (B). For some liposomes made by method (D) a double or half amount of RNA was used. The Z average particle diameter, polydispersity index and encapsulation efficiency of the liposomes were as follows:

| RV | Zav (nm) | pdI | % encapsulation | Preparation |
|---|---|---|---|---|
| RV01 (10) | 158.6 | 0.088 | 90.7 | (A) |
| RV01 (08) | 156.8 | 0.144 | 88.6 | (A) |
| RV01 (05) | 136.5 | 0.136 | 99 | (B) |
| RV01 (09) | 153.2 | 0.067 | 76.7 | (A) |
| RV01 (10) | 134.7 | 0.147 | 87.8 * | (A) |
| RV13 (02) | 128.3 | 0.179 | 97 | (A) |

* For this RV01(10) formulation the nucleic acid was DNA not RNA

Serum was collected for antibody analysis on days 14, 36 and 49. Spleens were harvested from mice at day 49 for T cell analysis.

F-specific serum IgG titers (GMT) were as follows:

| RV | Day 14 | Day 36 |
|---|---|---|
| Naked DNA plasmid | 439 | 6712 |
| Naked A317 RNA | 78 | 2291 |
| RV01 (10) | 3020 | 26170 |
| RV01 (08) | 2326 | 9720 |
| RV01 (05) | 5352 | 54907 |
| RV01 (09) | 4428 | 51316 |

-continued

| RV | Day 14 | Day 36 |
|---|---|---|
| RV01 (10) DNA | 5 | 13 |
| RV13 (02) | 644 | 3616 |

The proportion of T cells which are cytokine-positive and specific for RSV F51-66 peptide are as follows, showing only figures which are statistically significantly above zero:

| | CD4+CD8− | | | | CD4−CD8+ | | | |
|---|---|---|---|---|---|---|---|---|
| RV | IFNγ | IL2 | IL5 | TNFα | IFNγ | IL2 | IL5 | TNFα |
| Naked DNA plasmid | 0.04 | 0.07 | | 0.10 | 0.57 | 0.29 | | 0.66 |
| Naked A317 RNA | 0.04 | 0.05 | | 0.08 | 0.57 | 0.23 | | 0.67 |
| RV01 (10) | 0.07 | 0.10 | | 0.13 | 1.30 | 0.59 | | 1.32 |
| RV01 (08) | 0.02 | 0.04 | | 0.06 | 0.46 | 0.30 | | 0.51 |
| RV01 (05) | 0.08 | 0.12 | | 0.15 | 1.90 | 0.68 | | 1.94 |
| RV01 (09) | 0.06 | 0.08 | | 0.09 | 1.62 | 0.67 | | 1.71 |
| RV01 (10) DNA | | | | 0.03 | | | | 0.08 |
| RV13 (02) | 0.03 | 0.04 | | 0.06 | 1.15 | 0.41 | | 1.18 |

Thus the liposome formulations significantly enhanced immunogenicity relative to the naked RNA controls, as determined by increased F-specific IgG titers and T cell frequencies. Plasmid DNA formulated with liposomes, or delivered naked using electroporation, was significantly less immunogenic than liposome-formulated self-replicating RNA.

The RV01 RNA vaccines were more immunogenic than the RV13 vaccine. RV01 has a tertiary amine in the headgroup with a pKa of about 5.8, and also include unsaturated alkyl tails. RV13 has unsaturated alkyl tails but its headgroup has a quaternary amine and is very strongly cationic.

Liposomes—Requirement for Encapsulation

Figure 10:
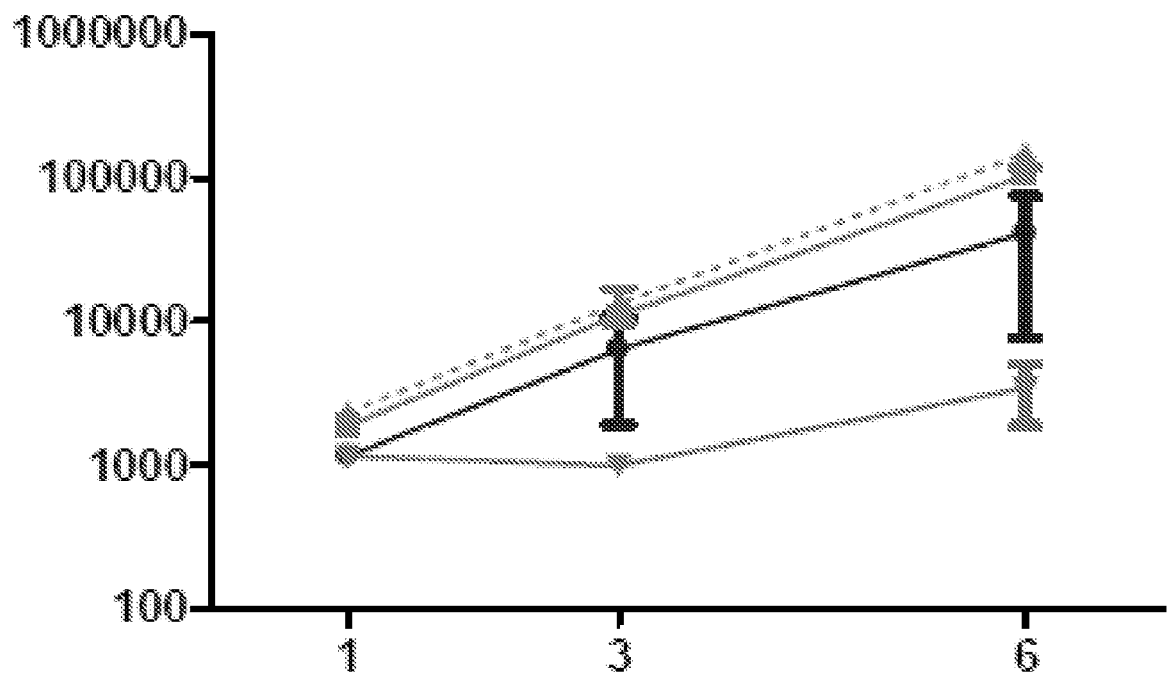
FIG. 10 shows expression levels after delivery of a replicon as naked RNA (circles), liposome-encapsulated RNA (triangle & square), or as a lipoplex (inverted triangle).

To assess whether the effect seen in the liposome groups was due merely to the liposome components, or was linked to the encapsulation, the replicon was administered in encapsulated form (with two different purification protocols, 0.1 μg RNA), or mixed with the liposomes after their formation (a non-encapsulated "lipoplex", 0.1 μg RNA), or as naked RNA (1 μg). FIG. 10 shows that the lipoplex gave the lowest levels of expression, showing that shows encapsulation is essential for potent expression.

Further experiments used three different RNAs: (i) 'vA317' replicon that expresses RSV-F i.e. the surface fusion glycoprotein of RSV; (ii) 'vA17' replicon that expresses GFP; and (iii) 'vA336' that is replication-defective and encodes GFP.

RNAs were delivered either naked or with liposomes made by method (D). Empty liposomes were made by method (D) but without any RNA. Four liposome formulations had these characteristics:

| RNA | Particle Size Zav (nm) | Polydispersity | RNA Encapsulation |
|---|---|---|---|
| vA317 | 155.7 | 0.113 | 86.6% |
| vA17 | 148.4 | 0.139 | 92% |
| vA336 | 145.1 | 0.143 | 92.9% |
| Empty | 147.9 | 0.147 | — |

BALB/c mice, 5 animals per group, were given bilateral intramuscular vaccinations (50 μL per leg) on days 0 and 21 with:
Group 1 naked self-replicating RSV-F RNA (vA317, 0.1 μg)
Group 2 self-replicating RSV-F RNA (vA317, 0.1 μg) encapsulated in liposomes
Group 3 self-replicating RSV-F RNA (vA317, 0.1 μg) added to empty liposomes
Group 4 F subunit protein (5 μg)

Serum was collected for antibody analysis on days 14, 35 and 51. F-specific specific serum IgG titers (GMT) were measured; if an individual animal had a titer of <25 (limit of detection), it was assigned a titer of 5. In addition, spleens were harvested from mice at day 51 for T cell analysis, to determine cells which were cytokine-positive and specific for RSV F51-66 peptide (CD4+) or for RSV F peptides F85-93 and F249-258 (CD8+).

IgG titers were as follows in the 10 groups and in non-immunised control mice:

| Day | 1 | 2 | 3 | 4 | — |
|---|---|---|---|---|---|
| 14 | 22 | 1819 | 5 | 5 | 5 |
| 35 | 290 | 32533 | 9 | 19877 | 5 |
| 51 | 463 | 30511 | 18 | 20853 | 5 |

RSV serum neutralization titers at day 51 were as follows:

| Day | 1 | 2 | 3 | 4 |
|---|---|---|---|---|
| 51 | 35 | 50 | 24 | 38 |

Animals showing RSV F-specific CD4+ splenic T cells on day 51 were as follows, where a number (% positive cells) is given only if the stimulated response was statistically significantly above zero:

| Cytokine | 1 | 2 | 3 | 4 |
|---|---|---|---|---|
| IFN-γ | | 0.04 | | |
| IL2 | 0.02 | 0.06 | | 0.02 |
| IL5 | | | | |
| TNFα | 0.03 | 0.05 | | |

Animals showing RSV F-specific CD8+ splenic T cells on day 51 were as follows, where a number is given only if the stimulated response was statistically significantly above zero:

| Cytokine | 1 | 2 | 3 | 4 |
|---|---|---|---|---|
| IFN-γ | 0.37 | 0.87 | | |
| IL2 | 0.11 | 0.40 | | 0.04 |
| IL5 | | | | |
| TNFα | 0.29 | 0.79 | | 0.06 |

Thus encapsulation of RNA within the liposomes is necessary for high immunogenicity, as a simple admixture of RNA and the liposomes (group 3) was not immunogenic (in fact, less immunogenic than naked RNA).

In other studies mice received various combinations of (i) self-replicating RNA replicon encoding full-length RSV F protein (ii) self-replicating GFP-encoding RNA replicon (iii)

GFP-encoding RNA replicon with a knockout in nsP4 which eliminates self-replication (iv) full-length RSV F-protein. 13 groups in total received:

| | | |
|---|---|---|
| A | — | — |
| B | 0.1 µg of (i), naked | — |
| C | 0.1 µg of (i), encapsulated in liposome | — |
| D | 0.1 µg of (i), with separate liposomes | — |
| E | 0.1 µg of (i), naked | 10 µg of (ii), naked |
| F | 0.1 µg of (i), naked | 10 µg of (iii), naked |
| G | 0.1 µg of (i), encapsulated in liposome | 10 µg of (ii), naked |
| H | 0.1 µg of (i), encapsulated in liposome | 10 µg of (iii), naked |
| I | 0.1 µg of (i), encapsulated in liposome | 1 µg of (ii), encapsulated in liposome |
| J | 0.1 µg of (i), encapsulated in liposome | 1 µg of (iii), encapsulated in liposome |
| K | 5 µg F protein | — |
| L | 5 µg F protein | 1 µg of (ii), encapsulated in liposome |
| M | 5 µg F protein | 1 µg of (iii), encapsulated in liposome |

Figure 16:
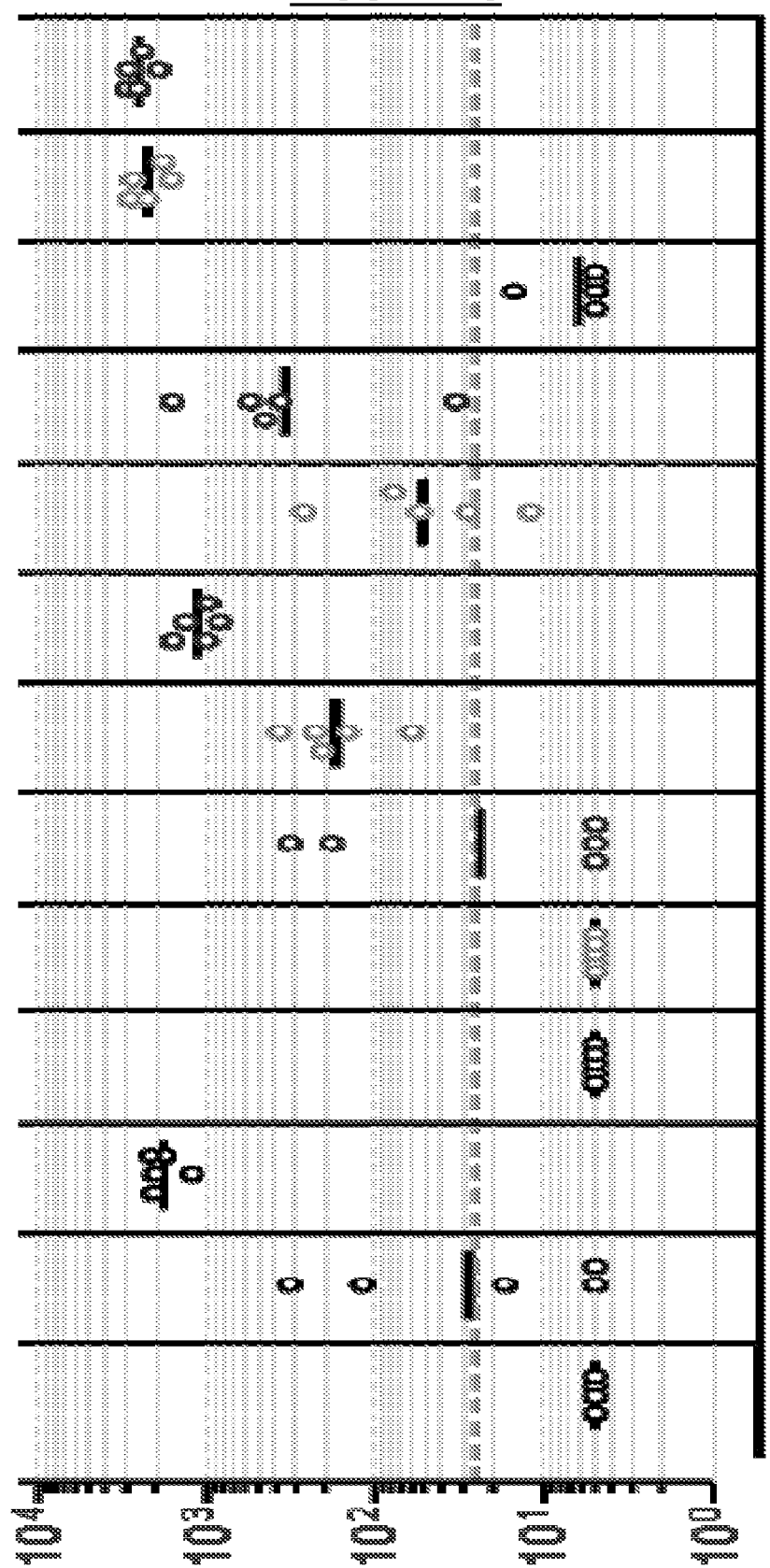
FIG. 16 shows IgG titers in 13 groups of mice. Each circle is an individual mouse, and solid lines show geometric means. The dotted horizontal line is the assay's detection limit. The 13 groups are, from left to right, A to M as described below.

Results in FIG. 16 show that F-specific IgG responses required encapsulation in the liposome rather than mere co-delivery (compare groups C & D). A comparison of groups K, L and M shows that the RNA provided an adjuvant effect against co-delivered protein, and this effect was seen with both replicating and non-replicating RNA.

RSV Immunogenicity in Different Mouse Strains

Replicon "vA142" encodes the full-length wild type surface fusion (F) glycoprotein of RSV but with the fusion peptide deleted, and the 3' end is formed by ribozyme-mediated cleavage. It was tested in three different mouse strains.

BALB/c mice were given bilateral intramuscular vaccinations (50 µL per leg) on days 0 and 22. Animals were divided into 8 test groups (5 animals per group) and a naïve control (2 animals):

Group 1 were given naked replicon (1 µg).
Group 2 were given 1 µg replicon delivered in liposomes "RV01(37)" with 40% DlinDMA, 10% DSPC, 48% Chol, 2% PEG-conjugated DMG.
Group 3 were given the same as group 2, but at 0.1 µg RNA.
Group 4 were given 1 µg replicon in "RV17(10)" liposomes (40% RV17 (see above), 10% DSPC, 49.5% cholesterol, 0.5% PEG-DMG).
Group 5 were 1 µg replicon in "RV05(11)" liposomes (40% RV07 lipid, 30% 18:2 PE (DLoPE, 28% cholesterol, 2% PEG-DMG).
Group 6 were given 0.1 µg replicon in "RV17(10)" liposomes.
Group 7 were given 5 µg RSV-F subunit protein adjuvanted with aluminium hydroxide.
Group 8 were a naïve control (2 animals)

Sera were collected for antibody analysis on days 14, 35 and 49. F-specific serum IgG GMTs were:

| Day | 1 | 2 | 3 | 4 | 5 | 6 | 7 | 8 |
|---|---|---|---|---|---|---|---|---|
| 14 | 82 | 2463 | 1789 | 2496 | 1171 | 1295 | 1293 | 5 |
| 35 | 1538 | 34181 | 25605 | 23579 | 13718 | 8887 | 73809 | 5 |

At day 35 F-specific IgG1 and IgG2a titers (GMT) were as follows:

| IgG | 1 | 2 | 3 | 4 | 5 | 6 | 7 |
|---|---|---|---|---|---|---|---|
| IgG1 | 94 | 6238 | 4836 | 7425 | 8288 | 1817 | 78604 |
| IgG2a | 5386 | 77064 | 59084 | 33749 | 14437 | 17624 | 24 |

RSV serum neutralizing antibody titers at days 35 and 49 were as follows (data are 60% plaque reduction neutralization titers of pools of 2-5 mice, 1 pool per group):

| Day | 1 | 2 | 3 | 4 | 5 | 6 | 7 | 8 |
|---|---|---|---|---|---|---|---|---|
| 35 | <20 | 143 | 20 | 101 | 32 | 30 | 111 | <20 |
| 49 | <20 | 139 | <20 | 83 | 41 | 32 | 1009 | <20 |

Spleens were harvested at day 49 for T cell analysis. Average net F-specific cytokine-positive T cell frequencies (CD4+ or CD8+) were as follows, showing only figures which were statistically significantly above zero (specific for RSV peptides F51-66, F164-178, F309-323 for CD4+, or for peptides F85-93 and F249-258 for CD8+):

| | CD4+CD8− | | | | CD4−CD8+ | | | |
|---|---|---|---|---|---|---|---|---|
| Group | IFNγ | IL2 | IL5 | TNFα | IFNγ | IL2 | IL5 | TNFα |
| 1 | 0.03 | 0.06 | | 0.08 | 0.47 | 0.29 | | 0.48 |
| 2 | 0.05 | 0.10 | | 0.08 | 1.35 | 0.52 | | 1.11 |
| 3 | 0.03 | 0.07 | | 0.06 | 0.64 | 0.31 | | 0.61 |
| 4 | 0.05 | 0.09 | | 0.07 | 1.17 | 0.65 | | 1.09 |
| 5 | 0.03 | 0.08 | | 0.07 | 0.65 | 0.28 | | 0.58 |
| 6 | 0.05 | 0.07 | | 0.07 | 0.74 | 0.36 | | 0.66 |
| 7 | | 0.02 | | | 0.04 | 0.04 | | |
| 8 | | | | | | | | |

C57BL/6 mice were immunised in the same way, but a 9th group received VRPs (1×10⁶ IU) expressing the full-length wild-type surface fusion glycoprotein of RSV (fusion peptide deletion).

Sera were collected for antibody analysis on days 14, 35 & 49. F-specific IgG titers (GMT) were:

| Day | 1 | 2 | 3 | 4 | 5 | 6 | 7 | 8 | 9 |
|---|---|---|---|---|---|---|---|---|---|
| 14 | 1140 | 2133 | 1026 | 2792 | 3045 | 1330 | 2975 | 5 | 1101 |
| 35 | 1721 | 5532 | 3184 | 3882 | 9525 | 2409 | 39251 | 5 | 12139 |

At day 35 F-specific IgG1 and IgG2a titers (GMT) were as follows:

| IgG | 1 | 2 | 3 | 4 | 5 | 6 | 7 | 8 |
|---|---|---|---|---|---|---|---|---|
| IgG1 | 66 | 247 | 14 | 328 | 468 | 92 | 56258 | 79 |
| IgG2a | 2170 | 7685 | 5055 | 6161 | 1573 | 2944 | 35 | 14229 |

RSV serum neutralizing antibody titers at days 35 and 49 were as follows (data are 60% plaque reduction neutralization titers of pools of 2-5 mice, 1 pool per group):

| Day | 1 | 2 | 3 | 4 | 5 | 6 | 7 | 8 | 9 |
|---|---|---|---|---|---|---|---|---|---|
| 35 | <20 | 27 | 29 | 22 | 36 | <20 | 28 | <20 | <20 |
| 49 | <20 | 44 | 30 | 23 | 36 | <20 | 33 | <20 | 37 |

Spleens were harvested at day 49 for T cell analysis. Average net F-specific cytokine-positive T cell frequencies (CD8+) were as follows, showing only figures which were statistically significantly above zero (specific for RSV peptides F85-93 and F249-258):

| Group | CD4−CD8+ | | | |
|---|---|---|---|---|
| | IFNγ | IL2 | IL5 | TNFα |
| 1 | 0.42 | 0.13 | | 0.37 |
| 2 | 1.21 | 0.37 | | 1.02 |
| 3 | 1.01 | 0.26 | | 0.77 |
| 4 | 1.26 | 0.23 | | 0.93 |
| 5 | 2.13 | 0.70 | | 1.77 |
| 6 | 0.59 | 0.19 | | 0.49 |
| 7 | 0.10 | 0.05 | | |
| 8 | | | | |
| 9 | 2.83 | 0.72 | | 2.26 |

Nine groups of C3H/HeN mice were immunised in the same way. F-specific IgG titers (GMT) were:

| Day | 1 | 2 | 3 | 4 | 5 | 6 | 7 | 8 | 9 |
|---|---|---|---|---|---|---|---|---|---|
| 14 | 5 | 2049 | 1666 | 1102 | 298 | 984 | 3519 | 5 | 806 |
| 35 | 152 | 27754 | 19008 | 17693 | 3424 | 6100 | 62297 | 5 | 17249 |

At day 35 F-specific IgG1 and IgG2a titers (GMT) were as follows:

| IgG | 1 | 2 | 3 | 4 | 5 | 6 | 7 | 8 |
|---|---|---|---|---|---|---|---|---|
| IgG1 | 5 | 1323 | 170 | 211 | 136 | 34 | 83114 | 189 |
| IgG2a | 302 | 136941 | 78424 | 67385 | 15667 | 27085 | 3800 | 72727 |

RSV serum neutralizing antibody titers at days 35 and 49 were as follows:

| Day | 1 | 2 | 3 | 4 | 5 | 6 | 7 | 8 | 9 |
|---|---|---|---|---|---|---|---|---|---|
| 35 | <20 | 539 | 260 | 65 | 101 | 95 | 443 | <20 | 595 |
| 49 | <20 | 456 | 296 | 35 | 82 | 125 | 1148 | <20 | 387 |

Thus three different lipids (RV01, RV05, RV17; pKa 5.8, 5.85, 6.1) were tested in three different inbred mouse strains. For all 3 strains RV01 was more effective than RV17; for BALB/c and C3H strains RV05 was less effective than either RV01 or RV17, but it was more effective in B6 strain. In all cases, however, the liposomes were more effective than two cationic nanoemulsions which were tested in parallel.

CMV Immunogenicity

RV01 liposomes with DLinDMA as the cationic lipid were used to deliver RNA replicons encoding cytomegalovirus (CMV) glycoproteins. The "vA160" replicon encodes full-length glycoproteins H and L (gH/gL), whereas the "vA322" replicon encodes a soluble form (gHsol/gL). The two proteins are under the control of separate subgenomic promoters in a single replicon; co-administration of two separate vectors, one encoding gH and one encoding gL, did not give good results.

BALB/c mice, 10 per group, were given bilateral intra-muscular vaccinations (50 μL per leg) on days 0, 21 and 42 with VRPs expressing gH/gL ($1 \times 10^6$ IU), VRPs expressing gHsol/gL ($1 \times 10^6$ IU) and PBS as the controls. Two test groups received 1 μg of the vA160 or vA322 replicon formulated in liposomes (40% DlinDMA, 10% DSPC, 48% Chol, 2% PEG-DMG; made using method (D) but with 150 μg RNA batch size).

The vA160 liposomes had a Zav diameter of 168 nm, a pdI of 0.144, and 87.4% encapsulation. The vA322 liposomes had a Zav diameter of 162 nm, a pdI of 0.131, and 90% encapsulation.

The replicons were able to express two proteins from a single vector.

Sera were collected for immunological analysis on day 63 (3wp3). CMV neutralization titers (the reciprocal of the serum dilution producing a 50% reduction in number of positive virus foci per well, relative to controls) were as follows:

| gH/gL VRP | gHsol/gL VRP | gH/gL liposome | gHsol/gL liposome |
|---|---|---|---|
| 4576 | 2393 | 4240 | 10062 |

RNA expressing either a full-length or a soluble form of the CMV gH/gL complex thus elicited high titers of neutralizing antibodies, as assayed on epithelial cells. The average titers elicited by the liposome-encapsulated RNAs were at least as high as for the corresponding VRPs.

Repeat experiments confirmed that the replicon was able to express two proteins from a single vector. The RNA replicon gave a 3wp3 titer of 11457, compared to 5516 with VRPs.

Further experiments used different replicons in addition to vA160. The vA526 replicon expresses the CMV pentameric complex (gH-gL-UL128-UL130-UL-131) under the control of three subgenomic promoters: the first drives the expression of gH; the second drives expression of gL; the third drives the expression of the UL128-2A-UL130-2A-UL131 polyprotein, which contains two 2A cleavage sites between the three UL genes. The vA527 replicon expresses the CMV pentameric complex via three subgenomic promoters and two IRESs: the first subgenomic promoter drives the expression of gH; the second subgenomic promoter drives expression of gL; the third subgenomic promoter drives the expression of the UL128; UL130 is under the control of an EMCV IRES; UL131 is under control of an EV71 IRES. These three replicons were delivered by liposome (method (H), with 150 μg batch size) or by VRPs.

BALB/c mice, 10 groups of 10 animals, were given bilateral intramuscular vaccinations (50 μL per leg) on days 0, 21 and 42 with:
- Group 1 VRPs expressing gH FL/gL ($1\times10^6$ IU)
- Group 2 pentameric, 2A VRP ($1\times10^5$ IU)
- Group 3 pentameric, 2A VRP ($1\times10^6$ IU)
- Group 4 pentameric, IRES VRP ($1\times10^5$ IU)
- Group 5 self-replicating RNA vA160 (1 μg) formulated in liposomes
- Group 6 self-replicating RNA vA526 (1 μg) formulated in liposomes
- Group 7 self-replicating RNA vA527 (1 μg) formulated in liposomes
- Group 8 self-replicating RNA vA160 (1 μg) formulated in a cationic nanoemulsion
- Group 9 self-replicating RNA vA526 (1 μg) formulated in a cationic nanoemulsion
- Group 10 self-replicating RNA vA527 (1 μg) formulated in a cationic nanoemulsion.

Sera were collected for immunological analysis on days 21 (3wp1), 42 (3wp2) and 63 (3wp3).

CMV serum neutralization titers on days 21, 42 and 63 were:

| Vaccine Group | 3wp1 | 3wp2 | 3wp3 |
|---|---|---|---|
| 1 | 126 | 6296 | 26525 |
| 2 | N/A | N/A | 6769 |
| 3 | N/A | 3442 | 7348 |
| 4 | N/A | N/A | 2265 |
| 5 | 347 | 9848 | 42319 |
| 6 | 179 | 12210 | 80000 |
| 7 | 1510 | 51200 | 130000 |
| 8 | N/A | N/A | 845 |
| 9 | N/A | N/A | 228 |
| 10 | N/A | N/A | 413 |

Thus self-replicating RNA can be used to express multiple antigens from a single vector and to raise a potent and specific immune response. The replicon can express five antigens (CMV pentamric complex (gH-gL-UL128-UL130-UL-131) and raise a potent immune response. Self-replicating RNA delivered in liposomes was able to elicit high titers of neutralizing antibody, as assayed on epithelial cells, at all time points assayed (3wp1, 3wp2, and 3wp3). These responses were superior to the corresponding VRPs and to cationic nanoemulsions.

Delivery Volume

Hydrodynamic delivery employs the force generated by the rapid injection of a large volume of solution to overcome the physical barriers of cell membranes which prevent large and membrane-impermeable compounds from entering cells. This phenomenon has previously been shown to be useful for the intracellular delivery of DNA vaccines.

A typical mouse delivery volume for intramuscular injection is 50 μl into the hind leg, which is a relatively high volume for a mouse leg muscle. In contrast, a human intramuscular dose of ~0.5 ml is relatively small. If immunogenicity in mice would be volume-dependent then the replicon vaccines' efficacy might be due, at least in part, on hydrodynamic forces, which would not be encouraging for use of the same vaccines in humans and larger animals.

The vA317 replicon was delivered to BALB/c mice, 10 per group, by bilateral intramuscular vaccinations (5 or 50 per leg) on day 0 and 21:

- Group 1 received naked replicon, 0.2 μg in 50 μL per leg
- Group 2 received naked replicon, 0.2 μg in 5 μL per leg
- Group 3 received liposome-formulated replicon (0.2 μg, 50 μL per leg)
- Group 4 received liposome-formulated replicon (0.2 μg, 5 μL per leg)

Serum was collected for antibody analysis on days 14 and 35. F-specific serum IgG GMTs were:

| Day | 1 | 2 | 3 | 4 |
|---|---|---|---|---|
| 14 | 42 | 21 | 2669 | 2610 |
| 35 | 241 | 154 | 17655 | 18516 |

Thus immunogenicity of the formulated replicon did not vary according to the delivered volume, thus indicating that these RNA vaccines do not rely on hydrodynamic delivery for their efficacy.

Expression Kinetics

A self-replicating RNA replicon ("vA311") that expresses a luciferase reporter gene (luc) was used for studying the kinetics of protein expression after injection. BALB/c mice, 5 animals per group, received bilateral intramuscular vaccinations (50 μL per leg) on day 0 with:
- Group 1 DNA expressing luciferase, delivered using electroporation (10 μg)
- Group 2 self-replicating RNA (1 μg) formulated in liposomes
- Group 3 self-replicating RNA (1 μg) formulated with a cationic nanoemulsion
- Group 4 self-replicating RNA (1 μg) formulated with a cationic nanoemulsion
- Group 5 VRP ($1\times10^6$ IU) expressing luciferase Prior to vaccination mice were depilated. Mice were anesthetized (2% isoflurane in oxygen), hair was first removed with an electric razor and then chemical Nair. Bioluminescence data was then acquired using a Xenogen IVIS 200 imaging system (Caliper Life Sciences) on days 3, 7, 14, 21, 28, 35, 42, 49, 63 and 70. Five minutes prior to imaging mice were injected intraperitoneally with 8 mg/kg of luciferin solution. Animals were then anesthetized and transferred to the imaging system.

Image acquisition times were kept constant as bioluminescence signal was measured with a cooled CCD camera.

In visual terms, luciferase-expressing cells were seen to remain primarily at the site of RNA injection, and animals imaged after removal of quads showed no signal.

In quantitative terms, luciferase expression was measured as average radiance over a period of 70 days ($p/s/cm^2/sr$), and results were as follows for the 5 groups:

| Days | 1 | 2 | 3 | 4 | 5 |
|---|---|---|---|---|---|
| 3 | 8.69E+07 | 3.33E+06 | 2.11E+06 | 9.71E+06 | 1.46E+07 |
| 7 | 1.04E+08 | 8.14E+06 | 1.83E+07 | 5.94E+07 | 1.64E+07 |
| 14 | 8.16E+07 | 2.91E+06 | 9.22E+06 | 3.48E+07 | 8.49E+05 |
| 21 | 1.27E+07 | 3.13E+05 | 6.79E+04 | 5.07E+05 | 6.79E+05 |
| 28 | 1.42E+07 | 6.37E+05 | 2.36E+04 | 4.06E+03 | 2.00E+03 |
| 35 | 1.21E+07 | 6.12E+05 | 2.08E+03 | | |
| 42 | 1.49E+07 | 8.70E+05 | | | |
| 49 | 1.17E+07 | 2.04E+05 | | | |
| 63 | 9.69E+06 | 1.72E+03 | | | |
| 70 | 9.29E+06 | | | | |

The self-replicating RNA formulated with cationic nanoemulsions showed measurable bioluminescence at day 3, which peaked at day 7 and then reduced to background levels by days 28 to 35. When formulated in liposomes the RNA showed measurable bioluminescence at day 3, which peaked at day 7 and reduced to background levels by day 63. RNA delivered using VRPs showed enhanced bioluminescence at day 21 when compared to the formulated RNA, but expression had reduced to background levels by day 28. Electroporated DNA showed the highest level of bioluminescence at all time points measured and levels of bioluminescence did not reduce to background levels within the 70 days of the experiment.

Delivery Route

Figure 15:
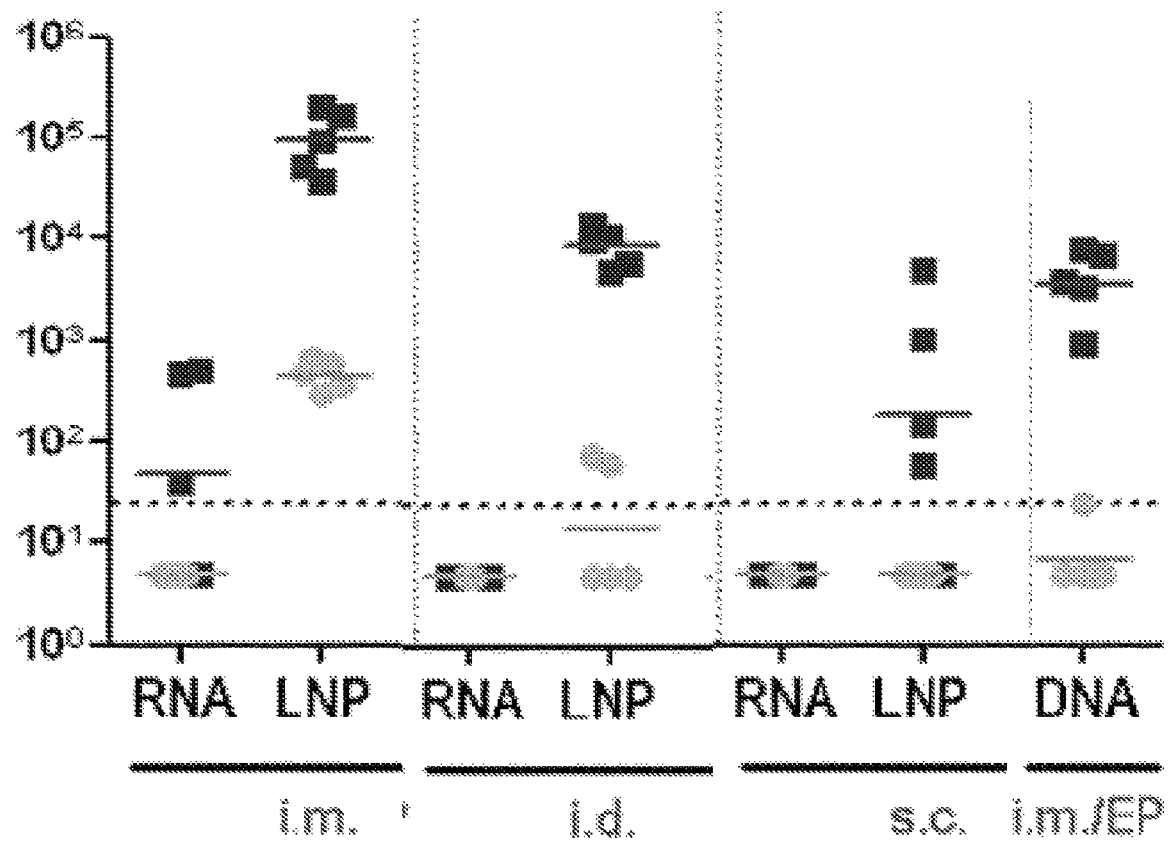
FIG. 15 shows anti-HIV serum IgG titers in response to naked ("RNA") or liposome-encapsulated ("LNP") RNA, or to DNA delivered by electroporated into muscle.

Liposome-encapsulated RNA encoding HIV gp140 was delivered to mice intramuscularly, intradermally, or subcutaneously. All three routes led to high serum IgG levels of HIV-specific antibodies (FIG. 15), exceeding titers seen in response to electroporated intramuscular DNA.

Cotton Rats

A study was performed in cotton rats (*Sigmodon hispidis*) instead of mice. At a 1 μg dose liposome encapsulation increased F-specific IgG titers by 8.3-fold compared to naked RNA and increased PRNT titers by 9.5-fold. The magnitude of the antibody response was equivalent to that induced by $5 \times 10^6$ IU VRP. Both naked and liposome-encapsulated RNA were able to protect the cotton rats from RSV challenge ($1 \times 10^5$ plaque forming units), reducing lung viral load by at least 3.5 logs. Encapsulation increased the reduction by about 2-fold.

Further work in cotton rats used four different replicons: vA317 expresses full-length RSV-F; vA318 expresses truncated (transmembrane and cytoplasmic tail removed) RSV-F; vA142 expresses RSV-F with its fusion peptide deleted; vA140 expresses the truncated RSV-F also without its peptide. Cotton rats, 4 to 8 animals per group, were given intramuscular vaccinations (100 μL in one leg) on days 0 and 21 with the four different replicons at two doses (1.0 and 0.1 μg) formulated in liposomes made by method (D), but with a 150 μg RNA batch size. Control groups received a RSV-F subunit protein vaccine (5 μg) adjuvanted with alum (8 animals/group), VRPs expressing full-length RSV-F ($1 \times 10^6$ IU, 8 animals/group), or naïve control (4 animals/group). Serum was collected for antibody analysis on days 0, 21 and 34.

F-specific serum IgG titers and RSV serum neutralizing antibody titers on day 21 and 34 were:

| Group | IgG, day 21 | IgG, day 34 | NT, day 21 | NT, day 34 |
|---|---|---|---|---|
| 1 μg vA317 | 915 | 2249 | 115 | 459 |
| 0.1 μg vA317 | 343 | 734 | 87 | 95 |
| 1 μg vA318 | 335 | 1861 | 50 | 277 |
| 0.1 μg vA318 | 129 | 926 | 66 | 239 |
| 1 μg vA142 | 778 | 4819 | 92 | 211 |
| 0.1 μg vA142 | 554 | 2549 | 78 | 141 |
| 1 μg vA140 | 182 | 919 | 96 | 194 |
| 0.1 μg vA140 | 61 | 332 | 29 | 72 |
| 5 μg F trimer subunit/alum | 13765 | 86506 | 930 | 4744 |
| $1 \times 10^6$ IU VRP-F full | 1877 | 19179 | 104 | 4528 |
| Naïve | 5 | 5 | 10 | 15 |

All four replicons evaluated in this study (vA317, vA318, vA142, vA140) were immunogenic in cotton rats when delivered by liposome, although serum neutralization titers were at least ten-fold lower than those induced by adjuvanted protein vaccines or by VRPs. The liposome/RNA vaccines elicited serum F-specific IgG and RSV neutralizing antibodies after the first vaccination, and a second vaccination boosted the response effectively. F-specific IgG titers after the second vaccination with 1 μg replicon were 2- to 3-fold higher than after the second vaccination with 0.1 μg replicon. The four replicons elicited comparable antibody titers, suggesting that full length and truncated RSV-F, each with or without the fusion peptide, are similarly immunogenic in cotton rats.

Further work in cotton rats again used the vA317, vA318 and vA142 replicons. Cotton rats, 2-8 animals per group, were given intramuscular vaccinations (100 μL in one leg) on days 0 and 21 with the replicons (0.1 or 1 μg) encapsulated in RV01 liposomes made by method (D) but with a 150 μg RNA batch size. Control groups received the RSV-F subunit protein vaccine (5 μg) adjuvanted with alum or VRPs expressing full-length RSV-F ($1 \times 10^6$ IU, 8 animals/group). All these animals received a third vaccination (day 56) with RSV-F subunit protein vaccine (5 μg) adjuvanted with alum. In addition there was a naïve control (4 animals/group). In addition, an extra group was given bilateral intramuscular vaccinations (50 μL per leg) on days 0 and 56 with 1 μg vA317 RNA in liposomes but did not receive a third vaccination with the subunit protein vaccine.

Serum was collected for antibody analysis on days 0, 21, 35, 56, 70, plus days 14, 28 & 42 for the extra group. F-specific serum IgG titers (GMT) were as follows:

| | Day 21 | Day 35 | Day 56 | Day 70 |
|---|---|---|---|---|
| 1 μg vA318 | 260 | 1027 | 332 | 14263 |
| 0.1 μg vA318 | 95 | 274 | 144 | 2017 |
| 1 μg vA142 | 483 | 1847 | 1124 | 11168 |
| 0.1 μg vA142 | 314 | 871 | 418 | 11023 |
| 1 μg vA317 | 841 | 4032 | 1452 | 13852 |
| $1 \times 10^6$ VRP (F-full) | 2075 | 3938 | 1596 | 14574 |
| 5 μg F trimer subunit/alum | 12685 | 54526 | 25846 | 48864 |
| Naïve | 5 | 5 | 5 | 5 |

Serum neutralisation titers were as follows (60% RSV neutralization titers for 2 pools of 3-4 animals per group, GMT of these 2 pools per group):

| | Day 21 | Day 35 | Day 56 | Day 70 |
|---|---|---|---|---|
| 1 μg vA318 | 58 | 134 | 111 | 6344 |
| 0.1 μg vA318 | 41 | 102 | 63 | 6647 |
| 1 μg vA142 | 77 | 340 | 202 | 5427 |
| 0.1 μg vA142 | 35 | 65 | 56 | 2223 |
| 1 μg vA317 | 19 | 290 | 200 | 4189 |
| $1 \times 10^6$ VRP (F-full) | 104 | 1539 | 558 | 2876 |
| 5 μg F trimer subunit/alum | 448 | 4457 | 1630 | 3631 |
| Naïve | 10 | 10 | 10 | |

Serum titers and neutralising titers for the extra group were as follows:

| Day | 14 | 21 | 28 | 35 | 42 | 56 | 70 |
|---|---|---|---|---|---|---|---|
| IgG | 397 | 561 | 535 | 501 | 405 | 295 | 3589 |
| NT | 52 | 82 | 90 | 106 | 80 | 101 | 1348 |

Thus the replicons are confirmed as immunogenic in cotton rats, eliciting serum F-specific IgG and RSV neutralizing antibodies after the first vaccination. A second vaccination boosted the responses effectively. F-specific IgG titers after the second vaccination with 1.0 μg replicon were 1.5 to 4-fold higher than after the second vaccination with 0.1 μg replicon.

The third vaccination (protein at day 56) did not boost titers in cotton rats previously vaccinated with F trimer subunit+alum, but it did provide a large boost to titers in cotton rats previously vaccinated with replicon. In most cases the RSV serum neutralization titers after two replicon vaccinations followed by protein boost were equal to or greater than titers induced by two or three sequential protein vaccinations.

This study also evaluated the kinetics of the antibody response to 1.0 µg vA317. F-specific serum IgG and RSV neutralization titers induced by a single vaccination reached their peak around day 21 and were maintained through at least day 56 (50-70% drop in F-specific IgG titer, little change in RSV neutralization titer). A homologous second vaccination was given to these animals on day 56, and boosted antibody titers to a level at least equal to that achieved when the second vaccination was administered on day 21.

Further experiments involved a viral challenge. The vA368 replicon encodes the full-length wild type surface fusion glycoprotein of RSV with the fusion peptide deleted, with expression driven by the EV71 IRES. Cotton rats, 7 per group, were given intramuscular vaccinations (100 µL per leg) on days 0 and 21 with vA368 in liposomes prepared by method (H), 175 µg RNA batch size, or with VRPs having the same replicon. A control group received 5 µg alum-adjuvanted protein, and a naïve control group was also included.

All groups received an intranasal challenge (i.n.) with $1 \times 10^6$ PFU RSV four weeks after the final immunization. Serum was collected for antibody analysis on days 0, 21, 35. Viral lung titers were measured 5 days post challenge. Results were as follows:

|  | Liposome | VRP | Protein | Naïve |
|---|---|---|---|---|
| F-specific Serum IgG titers (GMT) | | | | |
| Day 21 | 370 | 1017 | 28988 | 5 |
| Day 35 | 2636 | 2002 | 113843 | 5 |
| Neutralising titers (GMT) | | | | |
| Day 21 | 47 | 65 | 336 | 10 |
| Day 35 | 308 | 271 | 5188 | 10 |

|  | Liposome | VRP | Protein | Naïve |
|---|---|---|---|---|
| Lung viral load (pfu per gram of lung) | | | | |
| Day 54 | 422 | 225 | 124 | 694110 |

Thus the RNA vaccine reduced the lung viral load by over three logs, from approximately $10^6$ PFU/g in unvaccinated control cotton rats to less than $10^3$ PFU/g in vaccinated cotton rats.

Large Mammal Study

A large-animal study was performed in cattle. Calves (4-6 weeks old, ~60-80 kg, 5 per group) were immunised with 66 µg of replicon vA317 encoding full-length RSV F protein at days 0, 21, 86 and 146. The replicons were formulated inside liposomes. PBS alone was used as a negative control, and a licensed vaccine was used as a positive control ("Triangle 4" from Fort Dodge, containing killed virus). All calves received 15 µg F protein adjuvanted with the MF59 emulsion on day 146. One cow was mistakenly vaccinated with the wrong vaccine on day 86 instead of Triangle 4 and so its data were excluded from day 100 onwards.

The RNA vaccines encoded human RSV F whereas the "Triangle 4" vaccine contains bovine RSV F, but the RSV F protein is highly conserved between BRSV and HRSV.

The liposomes were made by method (E), except a 1.5 mg RNA batch size was used.

Calves received 2 ml of each experimental vaccine, administered intramuscularly as 2×1 ml on each side of the neck. In contrast, the "Triangle 4" vaccine was given as a single 2 ml dose in the neck.

Serum was collected for antibody analysis on days 0, 14, 21, 35, 42, 56, 63, 86, 100, 107, 114, 121, 128, 135, 146, 160, 167, 174, 181, 188, 195, and 202. If an individual animal had a titer below the limit of detection it was assigned a titer of 5

FIG. 14A shows F-specific IgG titers over the first 63 days. The RNA replicon was immunogenic in the cows via liposomes, although it gave lower titers than the licensed vaccine. All vaccinated cows showed F-specific antibodies after the second dose, and titers were very stable from the period of 2 to 6 weeks after the second dose (and were particularly stable for the RNA vaccines).

Figure 14B:
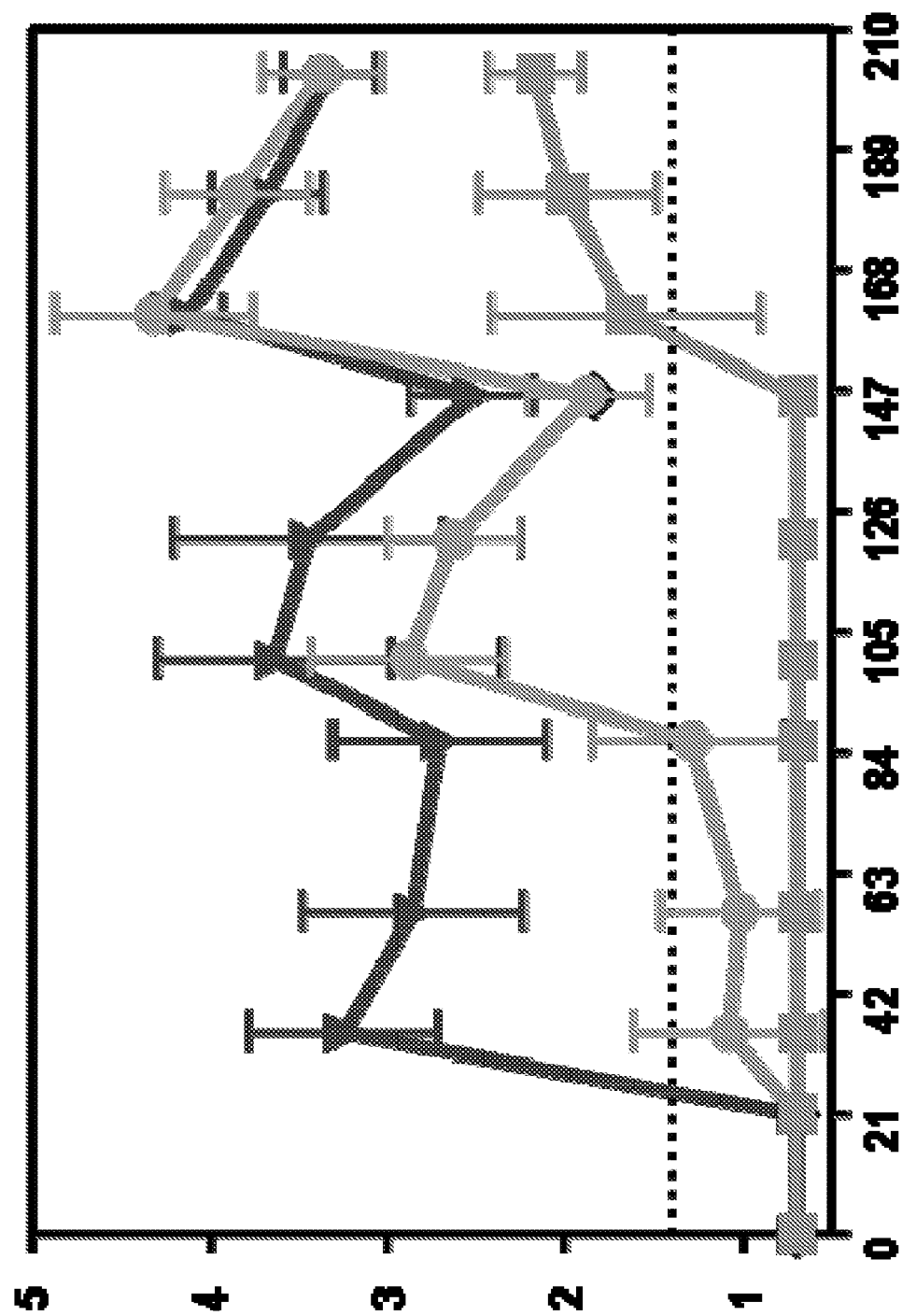
FIG. 14 shows F-specific IgG titers (mean $\log_{10}$ titers±std dev) over 63 days (FIG. 14A) and 210 days (FIG. 14B) after immunisation of calves. The three lines are easily distinguished at day 63 and are, from bottom to top: PBS negative control; liposome-delivered RNA; and the "Triangle 4" product.

FIG. 14B shows F-specific serum IgG titers (GMT) over 210 days, and measured values up to day 202 were as follows:

|  | D 0 | 3wp1 D 21 | 2wp2 D 35 | 5wp2 D 56 | ~9wp2 D 86 | 2wp3 D 100 | 5wp3 D 121 | 8wp3 D 146 | 2wp4 D 160 | 5wp4 D 181 | 8wp4 D 202 |
|---|---|---|---|---|---|---|---|---|---|---|---|
| PBS | 5 | 5 | 5 | 5 | 5 | 5 | 5 | 5 | 46 | 98 | 150 |
| Liposome | 5 | 5 | 12 | 11 | 20 | 768 | 428 | 74 | 20774 | 7022 | 2353 |
| Triangle 4 | 5 | 5 | 1784 | 721 | 514 | 3406 | 2786 | 336 | 13376 | 4775 | 2133 |

RSV serum neutralizing antibody titers were as follows:

|  | D 0 | 2wp2 D 35 | 5wp2 D 56 | 2wp3 D 100 | 3wp3 D 107 | 4wp3 D 114 | 8wp3 D 146 | 2wp4 D 160 | 3wp4 D 167 | 4wp4 D 174 |
|---|---|---|---|---|---|---|---|---|---|---|
| PBS | 12 | 10 | 10 | 14 | 18 | 20 | 14 | 10 | 10 | 10 |
| Liposome | 13 | 10 | 10 | 20 | 13 | 17 | 13 | 47 | 26 | 21 |
| Triangle 4 | 12 | 15 | 13 | 39 | 38 | 41 | 13 | 24 | 26 | 15 |

The material used for the second liposome dose was not freshly prepared, and the same lot of RNA showed a decrease in potency in a mouse immunogenicity study. Therefore it is possible that the vaccine would have been more immunogenic if fresh material had been used for all vaccinations.

When assayed with complement, neutralizing antibodies were detected in all vaccinated cows. In this assay, all vaccinated calves had good neutralizing antibody titers after the second RNA vaccination Furthermore, the RNA vaccine elicited F-specific serum IgG titers that were detected in a few calves after the second vaccination and in all calves after the third.

MF59-adjuvanted RSV-F was able to boost the IgG response in all previously vaccinated calves, and to boost complement-independent neutralization titers of calves previously vaccinated with RNA.

Proof of concept for RNA vaccines in large animals is particularly important in light of the loss in potency observed previously with DNA-based vaccines when moving from small animal models to larger animals and humans. A typical dose for a cow DNA vaccine would be 0.5-1 mg [47,48] and so it is very encouraging that immune responses were induced with only 66 µg of RNA.

It will be understood that the invention has been described by way of example only and modifications may be made whilst remaining within the scope and spirit of the invention.

TABLE 1

| useful phospholipids | |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidyl-rac-(1-glycerol . . .) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(1-glycerol . . .) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(1-glycerol . . .) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(1-glycerol . . .) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3[Phosphatidyl-rac-(1-glycerol . . .) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Diostearpyl-sn-Glycero-3-phosphatidylethanolamine |

TABLE 1-continued

| useful phospholipids | |
|---|---|
| DSPG | 1,2-Distearoyl-sn-Glycero-3[Phosphatidyl-rac-(1-glycerol . . .) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3[Phosphatidyl-rac-(1-glycerol . . .] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

REFERENCES

[1] Johanning et al. (1995) *Nucleic Acids Res* 23:1495-1501.
[2] Heyes et al. (2005) *J Controlled Release* 107:276-87.
[3] WO2005/121348.
[4] *Liposomes: Methods and Protocols, Volume 1: Pharmaceutical Nanocarriers: Methods and Protocols.* (ed. Weissig). Humana Press, 2009. ISBN 160327359X.
[5] *Liposome Technology,* volumes I, II & III. (ed. Gregoriadis). Informa Healthcare, 2006.
[6] *Functional Polymer Colloids and Microparticles volume 4 (Microspheres, microcapsules & liposomes).* (eds. Arshady & Guyot). Citus Books, 2002.
[7] Jeffs et al. (2005) *Pharmaceutical Research* 22 (3):362-372.
[8] *Polymers in Drug Delivery.* (eds. Uchegbu & Schatzlein). CRC Press, 2006.
[9] *Microparticulate Systems for the Delivery of Proteins and Vaccines.* (eds. Cohen & Bernstein). CRC Press, 1996.
[10] O'Hagan et al. (2001) *J Virology* 75:9037-9043.
[11] Singh et al. (2003) *Pharmaceutical Research* 20: 247-251.
[12] WO2009/132206.
[13] Martinon et al. (1993) *Eur J Immunol* 23:1719-22.
[14] WO2005/113782.
[15] WO2011/005799.
[16] El Ouahabi et al. (1996) *FEBS Letts* 380:108-12.
[17] Giuliani et al. (2006) *Proc Natl Acad Sci USA* 103(29): 10834-9.
[18] WO2009/016515.
[19] WO02/34771.
[20] WO2005/032582.
[21] WO2010/119343.

[22] WO2006/110413.
[23] WO2005/111066.
[24] WO2005/002619.
[25] WO2006/138004.
[26] WO2009/109860.
[27] WO02/02606.
[28] WO03/018054.
[29] WO2006/091517.
[30] WO2008/020330.
[31] WO2006/089264.
[32] WO2009/104092.
[33] WO2009/031043.
[34] WO2007/049155.
[35] Gennaro (2000) *Remington: The Science and Practice of Pharmacy.* 20th edition, ISBN: 0683306472.
[36] *Methods In Enzymology* (S. Colowick and N. Kaplan, eds., Academic Press, Inc.)
[37] *Handbook of Experimental Immunology*, Vols. I-IV (D. M. Weir and C. C. Blackwell, eds, 1986, Blackwell Scientific Publications)
[38] Sambrook et al. (2001) *Molecular Cloning: A Laboratory Manual*, 3rd edition (Cold Spring Harbor Laboratory Press).
[39] *Handbook of Surface and Colloidal Chemistry* (Birdi, K. S. ed., CRC Press, 1997)
[40] Ausubel et al. (eds) (2002) *Short protocols in molecular biology*, 5th edition (Current Protocols).
[41] *Molecular Biology Techniques: An Intensive Laboratory Course*, (Ream et al., eds., 1998, Academic Press)
[42] *PCR (Introduction to Biotechniques Series)*, 2nd ed. (Newton & Graham eds., 1997, Springer Verlag)
[43] Yoneyama & Fujita (2007) *Cytokine & Growth Factor Reviews* 18:545-51.
[44] Maurer et al. (2001) *Biophysical Journal*, 80: 2310-2326.
[45] Perri et al. (2003) *J Virol* 77:10394-10403.
[46] Iavarone et al. (2011) *J Immunol* 186; 4213-22.
[47] Boxus et al. (2007) *J Virol* 81:6879-89.
[48] Taylor et al. (2005) *Vaccine* 23:1242-50.

The invention claimed is:

1. A non-virion particle for in vivo delivery of RNA to a vertebrate cell, said particle comprising a delivery material and a self-replicating RNA molecule that encodes a polypeptide immunogen, wherein
   (a) said non-virion particle does not comprise a protein capsid, said delivery material is a liposome, and the RNA is encapsulated in the liposome (a "LNP");
   (b) the RNA molecule does not comprise modified nucleotides, other than a 5'cap, is not packaged with structural proteins as a virion, and cannot induce production of RNA-containing virions;
   (c) said non-virion particle can deliver RNA to a vertebrate cell in vivo; and
   (d) wherein the immunogen is translated in vivo and can elicit an immune response against said immunogen.

2. The particle of claim 1, wherein the self-replicating RNA molecule encodes (i) a RNA-dependent RNA polymerase which can transcribe RNA from the self-replicating RNA molecule and (ii) an immunogen.

3. The particle of claim 2, wherein the RNA molecule comprises two open reading frames, the first of which encodes an alphavirus replicase and the second of which encodes the immunogen.

4. The particle of claim 1, wherein the RNA molecule is 9000-12000 nucleotides long.

5. The particle of claim 1, wherein the immunogen can elicit an immune response in vivo against a bacterium, a virus, a fungus or a parasite.

6. The particle of claim 5, wherein the immunogen can elicit an immune response in vivo against respiratory syncytial virus glycoprotein F.

7. A pharmaceutical composition comprising a particle of claim 1.

* * * * *